United States Patent [19]
Abramson et al.

[11] Patent Number: 5,405,774
[45] Date of Patent: Apr. 11, 1995

[54] DNA ENCODING A MUTATED THERMOSTABLE NUCLEIC ACID POLYMERASE ENZIME FROM THERMUS SPECIES SPS17

[75] Inventors: Richard D. Abramson; David H. Gelfand, both of Oakland; I. Lawrence Greenfield, Pleasant Hill, all of Calif.

[73] Assignee: Hoffmann-La Roche Inc., Nutley, N.J.

[21] Appl. No.: 119,754

[22] Filed: Sep. 10, 1993

Related U.S. Application Data

[63] Continuation-in-part of Ser. No. 590,213, Sep. 28, 1990, abandoned, which is a continuation-in-part of Ser. No. 523,394, May 15, 1990, Pat. No. 5,079,352, which is a continuation-in-part of Ser. No. 143,441, Jan. 12, 1988, abandoned, which is a continuation-in-part of Ser. No. 63,509, Jun. 17, 1987, Pat. No. 4,889,818, which is a continuation-in-part of Ser. No. 899,241, Aug. 22, 1986, abandoned.

[51] Int. Cl.⁶ .................. C12N 9/12; C12N 15/00; C12N 1/20
[52] U.S. Cl. .................. 435/252.3; 435/252.8; 435/320.1; 435/194; 536/23.2; 935/10; 935/14
[58] Field of Search .................. 435/194, 320.1, 252.3, 435/252.8; 536/23.2; 935/10, 14

[56] References Cited

U.S. PATENT DOCUMENTS 4,889,818  12/1989  Gelfand et al. ............ 435/194
4,965,188  10/1990  Mullis et al. ............ 435/6

FOREIGN PATENT DOCUMENTS 8906691  7/1989  WIPO.

OTHER PUBLICATIONS

Chien et al., Sep. 1976, "Deoxyribonucleic Acid Polmerase from the Extreme Thermophile Thermus Aquaticus" J. Bacteriology 127(3):1550-1557.
Kaledin et al., 1980, "Isolation and Properties of DNA Polymerase from Extremely Thermophilic Bacterium Thermus Aquaticus YT1" Biochem. 45(4):494-501.
Suggs et al., Nov. 1981, "Use of Synthetic Oligonucleotides as Hybridization Probes: Isolation of Cloned cDNA Sequences for Human Beta-2-Microglobulin" Proc. Natl. Acad. Sci. USA 78(11):6613-6617.
Young and Davis, Mar. 1983, "Efficient Isolation of Genes by Using Antibody Probes" Proc. Natl. Acad. Sci. USA 80:1194-1198.
Bernad et al., 1989, "A Conserved 3'-5' Exonuclease Active Site in Prokaryotic and Eukaryotic DNA Polymerases" Cell 59:219-228.
Lawyer et al., 1989 "Isolation, Characterization, and Expression in *Escherichia coli* of the DNA Polymerase Gene From Thermus Aquaticus" J. Biological Chemistry 264(11)6427-6437.
Leavitt and Ito, Jun. 1989, "T5 DNA Polymerase: Structural-Fuctional Relationships to Other DNA Polymerases" Prod. Natl. Acad. Sci. USA 86:4465-4469.
Degryse et al., 1978, "A Comparative Analysis of Extreme Thermophilic Bacteria Belonging to the Genus Thermus" Arch. Microbiol. 117:189-196.
Microbiology, Fifth Ed., 1986, pp. 41-49, edited by M. J. Pelczal, Jr. et al. published by McGraw-Hill Book (List continued on next page.)

*Primary Examiner*—Robert A. Wax
*Assistant Examiner*—Keith D. Hendricks
*Attorney, Agent, or Firm*—George M. Gould; Dennis P. Tramaloni; Stacey R. Sias

[57] ABSTRACT

A purified thermostable enzyme is derived from the bacterium Thermus species sps17. The enzyme has DNA polymerase activity, reverse transcriptase activity, and optionally, 5'→3' exonuclease activity. The enzyme can be native or recombinant, and can be used with selected primers and nucleoside triphosphates in a temperature-cycling chain reaction where at least one nucleic acid sequence is amplified in quantity from an existing sequence.

11 Claims, No Drawings

OTHER PUBLICATIONS

Company (New York) "The Characterization, Classification and Identification of Microorganisms".

Microbiology, Fourth Ed., 1990, pp. 11–19, edited by B. D. Davis et al., published by J. B. Lippincott Company (Philadelphia) "Evolution of Microbiology and of Microbes".

"Biochemical Taxonomy of the Genes Thermus", published in: Microbiology of Extreme Environments and its Potential for Biotechnology pp. 82, et seq., eds. M. S. DaCosta, J. C. Durate and R. A. D. Williams, a volume of The Proceedings of the Federation of European Microbiological Societies Symposium held in Troia, Portugal, 18–23 Sep. 1988, published by Elsevier Applied Science (London and New York).

Gelfand, D. H, PCR Technology, Principles and Applications for DNA Amplification, Chapter 2, Entitled "Taq DNA Polymerase" pp. 17–22 (1989), Ed. by H. A. Erlich.

DNA ENCODING A MUTATED THERMOSTABLE NUCLEIC ACID POLYMERASE ENZYME FROM THERMUS SPECIES SPS17

CROSS-REFERENCE TO RELATED APPLICATIONS

This is a continuation-in-part application of U.S. Ser. No. 590,213, filed Sep. 28, 1990, now abandoned, which is a continuation-in-part of Ser. No. 523,394, filed May 15, 1990, which issued as U.S. Pat. No. 5,079,352, which is a continuation-in-part of now abandoned Ser. No. 143,441, filed Jan. 12, 1988, which is a continuation-in-part of Ser. No. 063,509, filed Jun. 17, 1987, which issued as U.S. Pat. No. 4,889,818 and which is a continuation-in-part of now abandoned Ser. No. 899,241, filed Aug. 22, 1986.

BACKGROUND OF THE INVENTION

1. Field of the Invention

The present invention relates to a purified, thermostable DNA polymerase purified from the thermophilic bacteria Thermus species sps17 and means for isolating and producing the enzyme. Thermostable DNA polymerases are useful in many recombinant DNA techniques, especially nucleic acid amplification by the polymerase chain reaction (PCR).

2. Background Art

Extensive research has been conducted on the isolation of DNA polymerases from mesophilic microorganisms such as *E. Coli*. See, for example, Bessman et al., 1957, *J. Biol. Chem.* 223:171–177 and Buttin and Kornberg, 1966, *J. Biol. Chem.* 241:5419–5427.

Much less investigation has been made on the isolation and purification of DNA polymerases from thermophiles such as Thermus species sps17. Kaledin et al., 1980, *Biokhymiya* 45:644–651 disclose a six-step isolation and purification procedure of DNA polymerase from cells of *Thermus aquaticus* YT-1 strain. These steps involve isolation of crude extract, DEAE-cellulose chromatography, fractionation on hydroxyapatite, fractionation on DEAE-cellulose, and chromatography on single-strand DNA-cellulose. The molecular weight of the purified enzyme is reported as 62,000 daltons per monomeric unit.

A second purification scheme for a polymerase from *Thermus aquaticus* is described by Chien et al., 1976, *J. Bacteriol.* 127:1550–1557. In this process, the crude extract is applied to a DEAE-Sephadex column. The dialyzed pooled fractions are then subjected to treatment on a phosphocellulose column. The pooled fractions are dialyzed and bovine serum albumin (BSA) is added to prevent loss of polymerase activity. The resulting mixture is loaded on a DNA-cellulose column. The pooled material from the column is dialyzed and analyzed by gel filtration to have a molecular weight of about 63,000 daltons and by sucrose gradient centrifugation of about 68,000 daltons.

The use of thermostable enzymes, such as those prepared by Chien et al. and Kaledin et al., to amplify existing nucleic acid sequences in amounts that are large compared to the amount initially present was described U.S. Pat. Nos. 4,683,195 and 4,683,202, which describe the PCR process, both disclosures of which are incorporated herein by reference. Primers, template, nucleotide triphosphates, the appropriate buffer and reaction conditions, and polymerase are used in the PCR process, which involves denaturation of target DNA, hybridization of primers, and synthesis of complementary strands. The extension product of each primer becomes a template for the production of the desired nucleic acid sequence. The two patents disclose that, if the polymerase employed is a thermostable enzyme, then polymerase need not be added after every denaturation step, because heat will not destroy the polymerase activity.

U.S. Pat. No. 4,889,818, European Patent Publication No. 258,017 and PCT Publication No. 89/06691, the disclosures of which are incorporated herein by reference, all describe the isolation and recombinant expression of an ~94 kDa thermostable DNA polymerase from *Thermus aquaticus* and the use of that polymerase in PCR. Although *T. aquaticus* DNA polymerase is especially preferred for use in PCR and other recombinant DNA techniques, there remains a need for other thermostable polymerases.

Accordingly, there is a desire in the art to produce a purified, thermostable DNA polymerase that may be used to improve the PCR process described above and to improve the results obtained when using a thermostable DNA polymerase in other recombinant techniques such as DNA sequencing, nick-translation, and even reverse transcription. The present invention helps meet that need by providing recombinant expression vectors and purification protocols for a DNA polymerase from Thermus species sps17.

SUMMARY OF THE INVENTION

Accordingly, the present invention provides a purified thermostable enzyme that catalyzes combination of nucleoside triphosphates to form a nucleic acid strand complementary to a nucleic acid template strand. The purified enzyme is the DNA polymerase activity from Thermus species sps17 (Tsps17). This purified material may be used in a temperature-cycling amplification reaction wherein nucleic acid sequences are produced from a given nucleic acid sequence in amounts that are large compared to the amount initially present so that the sequences can be manipulated and/or analyzed easily.

The gene encoding Tsps17 DNA polymerase enzyme from Thermus species sps17 has also been identified and cloned and provides yet another means to prepare the thermostable enzyme of the present invention. In addition to the portions of the gene encoding the Tsps17 enzyme, derivatives of these gene portions encoding Tsps17 DNA polymerase activity are also provided.

The invention also encompasses a stable enzyme composition comprising a purified, thermostable Tsps17 enzyme as described above in a buffer containing one or more non-ionic polymeric detergents.

Finally, the invention provides a method of purification for the thermostable polymerase of the invention. This method involves preparing a crude extract from Thermus species sps17 or recombinant host cells, adjusting the ionic strength of the crude extract so that the DNA polymerase dissociates from nucleic acid in the extract, subjecting the extract to hydrophobic interaction chromatography, subjecting the extract to DNA binding protein affinity chromatography, and subjecting the extract to cation or anion or hydroxyapatite chromatography. In a preferred embodiment, these steps are performed sequentially in the order given above. The nucleotide binding protein affinity chromatography step is preferred for separating the DNA polymerase from endonuclease proteins.

DETAILED DESCRIPTION OF THE INVENTION

The present invention provides DNA sequences and expression vectors that encode Tsps17 DNA polymerase. To facilitate understanding of the invention, a number of terms are defined below.

The terms "cell", "cell line", and "cell culture" can be used interchangeably and all such designations include progeny. Thus, the words "transformants" or "transformed cells" include the primary transformed cell and cultures derived from that cell without regard to the number of transfers. All progeny may not be precisely identical in DNA content, due to deliberate or inadvertent mutations. Mutant progeny that have the same functionality as screened for in the originally transformed cell are included in the definition of transformants.

The term "control sequences" refers to DNA sequences necessary for the expression of an operably linked coding sequence in a particular host organism. The control sequences that are suitable for procaryotes, for example, include a promoter, optionally an operator sequence, a ribosome binding site, and possibly other sequences. Eucaryotic cells are known to utilize promoters, polyadenylation signals, and enhancers.

The term "expression system" refers to DNA sequences containing a desired coding sequence and control sequences in operable linkage, so that hosts transformed with these sequences are capable of producing the encoded proteins. To effect transformation, the expression system may be included on a vector; however, the relevant DNA may also be integrated into the host chromosome.

The term "gene" refers to a DNA sequence that comprises control and coding sequences necessary for the production of a recoverable bioactive polypeptide or precursor. The polypeptide can be encoded by a full length coding sequence or by any portion of the coding sequence so long as the enzymatic activity is retained.

The term "operably linked" refers to the positioning of the coding sequence such that control sequences will function to drive expression of the protein encoded by the coding sequence. Thus, a coding sequence "operably linked" to control sequences refers to a configuration wherein the coding sequences can be expressed under the direction of a control sequence.

The term "mixture" as it relates to mixtures containing Tsps17 polymerase refers to a collection of materials which includes Tsps17 polymerase but which can also include other proteins. If the Tsps17 polymerase is derived from recombinant host cells, the other proteins will ordinarily be those associated with the host. Where the host is bacterial, the contaminating proteins will, of course, be bacterial proteins.

The term "non-ionic polymeric detergents" refers to surface-active agents that have no ionic charge and that are characterized for purposes of this invention, by an ability to stabilize the Tsps17 enzyme at a pH range of from about 3.5 to about 9.5, preferably from 4 to 8.5.

The term "oligonucleotide" as used herein is defined as a molecule comprised of two or more deoxyribonucleotides or ribonucleotides, preferably more than three, and usually more than ten. The exact size will depend on many factors, which in turn depends on the ultimate function or use of the oligonucleotide. The oligonucleotide may be derived synthetically or by cloning.

The term "primer" as used herein refers to an oligonucleotide which is capable of acting as a point of initiation of synthesis when placed under conditions in which primer extension is initiated. An oligonucleotide "primer" may occur naturally, as in a purified restriction digest or be produced synthetically. Synthesis of a primer extension product which is complementary to a nucleic acid strand is initiated in the presence of four different nucleoside triphosphates and the Tsps17 thermostable enzyme in an appropriate buffer at a suitable temperature. A "buffer" includes cofactors (such as divalent metal ions) and salt (to provide the appropriate ionic strength), adjusted to the desired pH. For Tsps17 polymerase, the buffer preferably contains 1 to 3 mM of a magnesium salt, preferably $MgCl_2$, 50 to 200 mM of each nucleotide, and 0.2 to 1 mM of each primer, along with 50 mM KCl, 10 mM Tris buffer (pH 8.0–8.4), and 100 mg/ml gelatin (although gelatin is not required, and should be avoided in some applications, such as DNA sequencing).

A primer is single-stranded for maximum efficiency in amplification, but may alternatively be double-stranded. If double-stranded, the primer is first treated to separate its strands before being used to prepare extension products. The primer is usually an oligodeoxyribonucleotide. The primer must be sufficiently long to prime the synthesis of extension products in the presence of the polymerase enzyme. The exact length of a primer will depend on many factors, such as source of primer and result desired, and the reaction temperature must be adjusted depending on primer length and nucleotide sequence to ensure proper annealing of primer to template. Depending on the complexity of the target sequence, an oligonucleotide primer typically contains 15 to 35 nucleotides. Short primer molecules generally require lower temperatures to form sufficiently stable complexes with template.

A primer is selected to be "substantially" complementary to a strand of specific sequence of the template. A primer must be sufficiently complementary to hybridize with a template strand for primer elongation to occur. A primer sequence need not reflect the exact sequence of the template. For example, a non-complementary nucleotide fragment may be attached to the 5' end of the primer, with the remainder of the primer sequence being substantially complementary to the strand. Non-complementary bases or longer sequences can be interspersed into the primer, provided that the primer sequence has sufficient complementarity with the sequence of the template to hybridize and thereby form a template primer complex for synthesis of the extension product of the primer.

The terms "restriction endonucleases" and "restriction enzymes" refer to bacterial enzymes which cut double-stranded DNA at or near a specific nucleotide sequence.

The term "thermostable enzyme" refers to an enzyme which is stable to heat and is heat resistant and catalyzes (facilitates) combination of the nucleotides in the proper manner to form primer extension products that are complementary to a template nucleic acid strand. Generally, synthesis of a primer extension product begins at the 3' end of the primer and proceeds in the 5' direction along the template strand, until synthesis terminates.

The Tsps17 thermostable enzyme of the present invention satisfies the requirements for effective use in the amplification reaction known as the polymerase chain reaction or PCR. The Tsps17 enzyme does not become irreversibly denatured (inactivated) when subjected to the elevated temperatures for the time necessary to effect denaturation of double-stranded nucleic acids, a key step in the PCR process. Irreversible denaturation for purposes herein refers to permanent and complete loss of enzymatic activity. The heating conditions necessary for nucleic acid denaturation will depend, e.g., on the buffer salt concentration and the composition and length of the nucleic acids being denatured, but typically range from about 90° C. to about 105° C. for a time depending mainly on the temperature and the nucleic acid length, typically from a few seconds up to four minutes. Higher temperatures may be required as the buffer salt concentration and/or GC composition of the nucleic acid is increased. The Tsps17 enzyme does not become irreversibly denatured for relatively short exposures to temperatures of about 90° C.-100° C.

The Tsps17 thermostable enzyme has an optimum temperature at which it functions that is higher than about 45° C. Temperatures below 45° C. facilitate hybridization of primer to template, but depending on salt composition and concentration and primer composition and length, hybridization of primer to template can occur at higher temperatures (e.g., 45° C.-70° C.), which may promote specificity of the primer hybridization reaction. The Tsps17 enzyme exhibits activity over a broad temperature range from about 37° C. to 90° C.

The present invention provides DNA sequences encoding the thermostable DNA polymerase activity of Thermus species sps17. The gene coding sequence has homology to portions of the DNA sequences encoding the thermostable DNA polymerases of $T.$ aquaticus (Taq) strain YT1, $T.$ thermophilus (Tth), T. species Z05 (TZ05), Thermotoga maritima (Tma), and Thermosipho africanus (Taf). The entire Tsps17 polymerase gene (Seq ID No. 38) and the deduced amino acid sequence (Seq ID No. 2) is depicted below. For convenience, the amino acid sequence of this Tsps17 polymerase is numbered for reference. The coding sequence of the Tsps17 polymerase gene begins at nucleotide number 1246 and continues through base pair 3735 where the TGA stop codon is found (Seq ID No. 1). However, for completeness, portions of the 5' and 3' noncoding regions of the T. species sps17 DNA polymerase gene are also shown.

```
   1 TACCGGCGGATTCGGGTTTCTCTGGAAGAGGACCAGTGGATCCGG
  46 CTGAAAACCCTGGCCCAGGAGCTAAGCCAGAAGCGAGGCCGCCGG
  91 GTAAGTGCCAGCGAAGTCCTCCGTGAGCTTTTGGACAAAGGTCTT
 136 CGGGAGGTTTCCAGGAGCGAAGCCTTGAGGCGGCTTTCTTCCCTT
 181 AGGGGGCGGATTTCCTTGGAGGGCCTGAGTTTGGAGGGCCTTTTA
 226 GAAGAGGTGAGGGAGGGGCGTGTCCAAGATCTACTGGGTGGTTGA
 271 TGCTTCCCTTGCCCTAGCCCTTGTCCTGCCCCATCCGGCCCAGAA
 316 GGAGGCGGAGGCCTTCTGGCGGGAGGAGGCTCCAAAAGGTGAGGT
 361 GTGGGTGCCCCGGCTTTTTGCCGCGGAAGTGGCCTCGGTTCTCCG
 406 TGCCCTGGTGTTTGCCCGCAGGATGGCGCAAGGGGAGGCGGAAGA
 451 GCTCTTGGAGATCCTTTTAGAGCTTCCCGACCGCTTCGCCGAGGA
 496 TGAAGCTCTGGCCCTTCGGGCTTTGCGCTGGGCGGGGCTTTGGG
 541 GCAAAAGCGGGCCTACGACGCCTTTTACGTGGCCTTGGCGGAAGA
 586 GAAAGGGGCCCAGCTTTTGACGGTGGATTTGAAACTGGCCCACGC
 631 CCTGCACGCCCAGGGGGTGCCCTGGGTTCGGGCTTTAGGGGAGGC
 676 CGTATGACCTTGGCCGAACCTGTGGTGTACGAGGAGGTCATCGGG
 721 AAAAGCCGCTTCCTCGCCAAGGCGGCCCCCGTGGCCTCGGAGGAG
 766 GAGGCCCTGGCCTTCTTGGAATGGGCTTCGGAAAGGGAGGCCACC
 811 CACAACCCCTACGCCTACCGGATCGGCCCCCTTTACCGCTTCTCC
 856 GACGACGGGGAGCCCAGCGGCACCGCGGGCCGCCCCATCCTTCAC
 901 GCCATAGAGGCCCAGGGCCTGGACCGGGTGGCCGTGGTGGTGGTG
 946 CGCTACTTCGGGGGGGTGAAGCTCGGGGCGGGGGGGCTGGTGCGG
 991 GCCTACGGGGGGATGGCGGCGGAGGCCTTGAGGCGGGCGGGGAAG
1036 GTCCCCATCGTGGACTGGGCCGAGGCGGCCTTCCTGGTCCCTTTT
1081 GCCGAGGTGGGGGCGGCCTACCGGGCCCTTAGGGGCCTACCCGTG
1126 GCGGAGGAGTACCGGGAGGAAGGGGTCCTCCTGCGCCTGAGGCTT
1171 CCCAAGGACCGCCTCGAGGCCTTAGCCCAGGCCCTCACCGAGGCC
```

-continued

```
1216 ACCCGGGGCCGGGTCCGTAGAATGTGAGGGATGCTGCCCCTCTTT
   1                                          Met Leu Pro Leu Phe

1261 GAGCCCAAGGGCCGGGTCCTCCTGGTGGACGGCCACCACCTGGCC
   6 Glu Pro Lys Gly Arg Val Leu Leu Val Asp Gly His His Leu Ala

1306 TACCGCACCTTTTTCGCCCTCAAGGGCCTCACCACCAGCCGGGGC
  21 Tyr Arg Thr Phe Phe Ala Leu Lys Gly Leu Thr Thr Ser Arg Gly

1351 GAGCCCGTGCAGGCGGTTTATGGCTTCGCCAAAAGCCTCCTCAAG
  36 Glu Pro Val Gln Ala Val Tyr Gly Phe Ala Lys Ser Leu Leu Lys

1396 GCCCTGAAGGAGGATGGGGAGGTGGCCATCGTGGTCTTTGACGCC
  51 Ala Leu Lys Glu Asp Gly Glu Val Ala Ile Val Val Phe Asp Ala

1441 AAGGCCCCCTCCTTCCGCCACGAGGCCTACGAGGCCTACAAGGCG
  66 Lys Ala Pro Ser Phe Arg His Glu Ala Tyr Glu Ala Tyr Lys Ala

1486 GGCCGGGCCCCCACCCCGGAGGACTTTCCCCGGCAGCTCGCCCTC
  81 Gly Arg Ala Pro Thr Pro Glu Asp Phe Pro Arg Gln Leu Ala Leu

1531 ATCAAGGAGCTGGTGGACCTTTTGGGCCTCGTGCGCCTTGAGGTC
  96 Ile Lys Glu Leu Val Asp Leu Leu Gly Leu Val Arg Leu Glu Val

1576 CCGGGCTTTGAGGCGGACGATGTCCTCGCCACCCTGGCCAAGAAG
 111 Pro Gly Phe Glu Ala Asp Asp Val Leu Ala Thr Leu Ala Lys Lys

1621 GCAGAAAGGGAGGGGTACGAGGTGCGCATCCTGAGCGCGGACCGC
 126 Ala Glu Arg Glu Gly Tyr Glu Val Arg Ile Leu Ser Ala Asp Arg

1666 GACCTCTACCAGCTCCTTTCCGACCGGATCCACCTCCTCCACCCC
 141 Asp Leu Tyr Gln Leu Leu Ser Asp Arg Ile His Leu Leu His Pro

1711 GAGGGGGAGGTCCTGACCCCCGGGTGGCTCCAGGAGCGCTACGGC
 156 Glu Gly Glu Val Leu Thr Pro Gly Trp Leu Gln Glu Arg Tyr Gly

1756 CTCTCCCCGGAGAGGTGGGTGGAGTACCGGGCCCTGGTGGGGGAC
 171 Leu Ser Pro Glu Arg Trp Val Glu Tyr Arg Ala Leu Val Gly Asp

1801 CCTTCGGACAACCTCCCCGGGGTGCCCGGCATCGGGGAGAAGACC
 186 Pro Ser Asp Asn Leu Pro Gly Val Pro Gly Ile Gly Glu Lys Thr

1846 GCCCTGAAGCTCCTGAAGGAGTGGGGTAGCCTGGAAGCGATTCTA
 201 Ala Leu Lys Leu Leu Lys Glu Trp Gly Ser Leu Glu Ala Ile Leu

1891 AAGAACCTGGACCAGGTGAAGCCGGAAAGGGTGCGGGAGGCCATC
 216 Lys Asn Leu Asp Gln Val Lys Pro Glu Arg Val Arg Glu Ala Ile

1936 CGGAATAACCTGGATAAGCTCCAGATGTCCCTGGAGCTTTCCCGC
 321 Arg Asn Asn Leu Asp Lys Leu Gln Met Ser Leu Glu Leu Ser Arg

1981 CTCCGCACCGACCTCCCCCTGGAGGTGGACTTCGCCAAGAGGCGG
 246 Leu Arg Thr Asp Leu Pro Leu Glu Val Asp Phe Ala Lys Arg Arg

2026 GAGCCCGACTGGGAGGGGCTTAAGGCCTTTTTGGAGCGGCTTGAG
 261 Glu Pro Asp Trp Glu Gly Leu Lys Ala Phe Leu Glu Arg Leu Glu

2071 TTCGGAAGCCTCCTCCACGAGTTCGGCCTTCTGGAGGCCCCCAAG
 276 Phe Gly Ser Leu Leu His Glu Phe Gly Leu Leu Glu Ala Pro Lys

2116 GAGGCGGAGGAGGCCCCCTGGCCCCCGCCTGGAGGGGCCTTTTTG
 291 Glu Ala Glu Glu Ala Pro Trp Pro Pro Pro Gly Gly Ala Phe Leu

2161 GGCTTCCTCCTCTCCCGCCCCGAGCCCATGTGGGCGGAGCTTTTG
 306 Gly Phe Leu Leu Ser Arg Pro Glu Pro Met Trp Ala Glu Leu Leu

2206 GCCCTGGCGGGGGCCAAGGAGGGGCGGGTCCATCGGGCGGAAGAC
 321 Ala Leu Ala Gly Ala Lys Glu Gly Arg Val His Arg Ala Glu Asp

2251 CCCGTGGGGGCCCTAAAGGACCTGAAGGAGATCCGGGGCCTCCTC
 336 Pro Val Gly Ala Leu Lys Asp Leu Lys Glu Ile Arg Gly Leu Leu

2296 GCCAAGGACCTCTCGGTCCTGGCCCTGAGGGAGGGCCGGGAGATC
 351 Ala Lys Asp Leu Ser Val Leu Ala Leu Arg Glu Gly Arg Glu Ile

2341 CCGCCGGGGGACGACCCCATGCTCCTCGCCTACCTCCTGGACCCG
 366 Pro Pro Gly Asp Asp Pro Met Leu Leu Ala Tyr Leu Leu Asp Pro

2386 GGGAACACCAACCCCGAGGGGGTGGCCCGGCGGTACGGGGGGGAG
 381 Gly Asn Thr Asn Pro Glu Gly Val Ala Arg Arg Tyr Gly Gly Glu

2431 TGGAAGGAGGACGCCGCCGCCCGGGCCCTCCTTTCGGAAAGGCTC
```

| | | | | | | | | | | | | | | |
|---|---|---|---|---|---|---|---|---|---|---|---|---|---|---|
|396|Trp|Lys|Glu|Asp|Ala|Ala|Ala|Arg|Ala|Leu|Leu|Ser|Glu|Arg|Leu|

2476 TGGCAGGCCCTTTACCCCCGGGTGGCGGAGGAGGAAAGGCTCCTT
411 Trp Gln Ala Leu Tyr Pro Arg Val Ala Glu Glu Glu Arg Leu Leu

2521 TGGCTCTACCGGGAGGTGGAGCGGCCCCTCGCCCAGGTCCTCGCC
426 Trp Leu Tyr Arg Glu Val Glu Arg Pro Leu Ala Gln Val Leu Ala

2566 CACATGGAGGCCACGGGGGTGCGGCTGGATGTGCCCTACCTGGAG
441 His Met Glu Ala Thr Gly Val Arg Leu Asp Val Pro Tyr Leu Glu

2611 GCCCTTTCCCAGGAGGTGGCCTTTGAGCTGGAGCGCCTCGAGGCC
456 Ala Leu Ser Gln Glu Val Ala Phe Glu Leu Glu Arg Leu Glu Ala

2656 GAGGTCCACCGCCTGGCGGGCCACCCCTTCAACCTGAACTCTAGG
471 Glu Val His Arg Leu Ala Gly His Pro Phe Asn Leu Asn Ser Arg

2701 GACCAGCTGGAGCGGGTCCTCTTTGACGAGCTCGGCCTACCCCCC
486 Asp Gln Leu Glu Arg Val Leu Phe Asp Glu Leu Gly Leu Pro Pro

2746 ATCGGCAAGACGGAGAAGACGGGCAAGCGCTCCACCAGCGCCGCC
501 Ile Gly Lys Thr Glu Lys Thr Gly Lys Arg Ser Thr Ser Ala Ala

2791 GTCCTGGAGCTCTTAAGGGAGGCCCACCCCATCGTGGGGCGGATC
516 Val Leu Glu Leu Leu Arg Glu Ala His Pro Ile Val Gly Arg Ile

2836 CTGGAGTACCGGGAGCTCATGAAGCTCAAGAGCACCTACATAGAC
531 Leu Glu Tyr Arg Glu Leu Met Lys Leu Lys Ser Thr Tyr Ile Asp

2881 CCCCTCCCCAGGCTGGTCCACCCCAAAACCGGCCGGCTCCACACC
546 Pro Leu Pro Arg Leu Val His Pro Lys Thr Gly Arg Leu His Thr

2926 CGCTTCAACCAGACGGCCACCGCCACGGGCCGCCTCTCCAGCTCC
561 Arg Phe Asn Gln Thr Ala Thr Ala Thr Gly Arg Leu Ser Ser Ser

2971 GACCCCAACCTGCAGAACATCCCCGTGCGCACCCCCTTAGGCCAG
576 Asp Pro Asn Leu Gln Asn Ile Pro Val Arg Thr Pro Leu Gly Gln

3016 CGCATCCGCAAGGCCTTCATTGCCGAGGAGGGCCATCTCCTGGTG
591 Arg Ile Arg Lys Ala Phe Ile Ala Glu Glu Gly His Leu Leu Val

3061 GCCCTGGACTATAGCCAGATCGAGCTCCGGGTCCTCGCCCACCTC
606 Ala Leu Asp Tyr Ser Gln Ile Glu Leu Arg Val Leu Ala His Leu

3106 TCGGGGGACGAGAACCTCATCCGGGTCTTCCGGGAAGGGAAGGAC
621 Ser Gly Asp Glu Asn Leu Ile Arg Val Phe Arg Glu Gly Lys Asp

3151 ATCCACACCGAGACCGCCGCCTGGATGTTCGGCGTGCCCCCCGAG
636 Ile His Thr Glu Thr Ala Ala Trp Met Phe Gly Val Pro Pro Glu

3196 GGGGTGGACGGGGCCATGCGCCGGGCGGCCAAGACGGTGAACTTC
651 Gly Val Asp Gly Ala Met Arg Arg Ala Ala Lys Thr Val Asn Phe

3241 GGGGTGCTCTACGGGATGTCCGCCCACCGCCTCTCCCAGGAGCTC
666 Gly Val Leu Tyr Gly Met Ser Ala His Arg Leu Ser Gln Glu Leu

3286 TCCATCCCCTACGAGGAGGCGGCGGCCTTCATCGAGCGCTACTTC
681 Ser Ile Pro Tyr Glu Glu Ala Ala Ala Phe Ile Glu Arg Tyr Phe

3331 CAGAGCTTCCCCAAGGTGCGGGCCTGGATCGCCAAAACCTTGGAG
696 Gln Ser Phe Pro Lys Val Arg Ala Trp Ile Ala Lys Thr Leu Glu

3376 GAGGGGCGGAAGAAGGGGTACGTGGAGACCCTCTTCGGCCGCCGC
711 Glu Gly Arg Lys Lys Gly Tyr Val Glu Thr Leu Phe Gly Arg Arg

3421 CGCTACGTGCCCGACCTCAACGCCCGGGTGAAGAGCGTGCGGGAG
726 Arg Tyr Val Pro Asp Leu Asn Ala Arg Val Lys Ser Val Arg Glu

3466 GCGGCGGAGCGCATGGCCTTCAACATGCCCGTGCAGGGCACCGCC
741 Ala Ala Glu Arg Met Ala Phe Asn Met Pro Val Gln Gly Thr Ala

3511 GCGGACCTCATGAAGCTGGCCATGGTGAAGCTCTTCCCCAGGCTC
756 Ala Asp Leu Met Lys Leu Ala Met Val Lys Leu Phe Pro Arg Leu

3556 AGGCCCTTGGGCGTTCGCATCCTCCTCCAGGTGCACGACGAGCTG
771 Arg Pro Leu Gly Val Arg Ile Leu Leu Gln Val His Asp Glu Leu

3601 GTCTTGGAGGCCCCAAAGGCGCGGGCGGAGGAGGCCGCCCAGTTG
786 Val Leu Glu Ala Pro Lys Ala Arg Ala Glu Glu Ala Ala Gln Leu

3646 GCCAAGGAGACCATGGAAGGGGTTTACCCCCTCTCCGTCCCCCTG
801 Ala Lys Glu Thr Met Glu Gly Val Tyr Pro Leu Ser Val Pro Leu

```
3691 GAGGTGGAGGTGGGGATGGGGGAGGACTGGCTTTCCGCCAAGGCC
 816 Glu  Val  Glu  Val  Gly  Met  Gly  Glu  Asp  Trp  Leu  Ser  Ala  Lys  Ala

3736 TAGCCCCCCAAGCTCAGGAGGGTGTACAGGGCCACTCCTAGGAGG

3781 ATCGCCGCGCCCAGGTGGCCCGTGGCCCGGGCGGCGGCGTAGACC

3826 CCGAAGAGGCCCAGGGCCACCCGCGCCCACTCCGGGGAGGGTGGG

3871 GGGGAGAAGGCCGAAACCAGGAAGAGGGCCACCACCAGGCTGGGC

3916 CCCACCTGGCCCACCCCCAACCTCCGCCCCAGCGCCAGGGAAAG

3961 AGGCGTAGGAGATAGGTGCCCAGGGCCAGGAGCAGGAGGGCCAGG

4006 GTCAAGGCCTTCCTCCCCAAAGCCCGATGGCCCCCGCCAGGAGAA

4051 GGCCCAAGGCGGTTTCGCCCCCAAGGTGGCAGGCCAGGGCCACGC

4096 CCCCTGCCAGGAGGGCCACGGGGTTTTTCAGATGGGGAAGGGCGA

4141 GGAGGAAAAAGAGGGCGGGTAGGGCGAAGGTGAGGCCTTGGGCCA

4186 GGGCGGGGAAGGCCTTAAGCCCCTGGGCCCCAACGCCCCCGTCA

4231 GGGTGCCCAGGTTCCAGCTGGCGTAGGCCCCTAGGCCAAGGCCCA

4276 GGAAGAAGCCCGGCCGTTTCCCTTCGGGAAGCTCTGGAAGCCTGT

4321 GCAGGGCTAGGGCGAAGACCTCATCGGTGAGGAAAAAGGCGAGGA

4366 GGGGGCTTCCTGTCAGGTAGGGTTTGAGGACGGGGCCGTAGAAGG

4411 CGTGGCGGAGGTTGAGGAGGAGGGCGAGGAGGGCTGAAAGGAGGG

4456 GTGGGGTTCCCGTGGCGAGAAGCCCCACCAGGGCGAACTGGGCGG

4501 CCCCGGCAAAGACGAGAAGGGAGATGAGCGCCACCGTCCAGGGGG

4546 AAAGCCCGGCCCCTACCCCCAGCATCCCGAAGGCCACGGCCACCG

4591 GGAAATAGCCTAGGCCACGGGCCAGGCCGCTTGCAATCCTTCCTT

4636 CATGGGGAGGGATTTTATCCGAAGCGCTAGGATGGGATTGGAATG

4681 GCCCGCATCTGGCTCAACCTGGGGGCCAAGGTCCTGGAGGAGGCC

4726 CTGGCGGAGCGCCTGAAGGCCTTGGGGCACGAGGTGGTCCCGGAC

4771 CCCCAAAAGGCCCAGCTGGCCTTGGTCTTCCTCACCCACCTGGAG

4816 GGGCCGCCCCCCCTCCCCGCCACCCTGGCCCTCCTGGCCAGCCCC

4861 CACCTGGCGGAGGGGGCTTTGCGCCTGGGCTACCGGGGTACC
```

The above nucleotide sequence was identified by a "degenerate primer" method that has broad utility and is an important aspect of the present invention. In the degenerate primer method, DNA fragments of any thermostable polymerase coding sequence corresponding to conserved domains of known thermostable DNA polymerases can be identified.

The degenerate primer method was developed by comparing the amino acid sequences of DNA polymerase proteins from Taq, Tth, T7, and E. coli polymerase I in which various conserved regions were identified. Primers corresponding to these conserved regions were then designed. As a result of the present invention, Tsps17 sequences can be used to design other degenerate primers. The generic utility of the degenerate primer process is exemplified in Ser. No. 567,244, filed Aug. 13, 1990, Ser. No. 07/590,466, filed herewith at even date, and Ser. No. 07/590,490, filed herewith at even date, each of which is incorporated herein by reference. The same process described in these applications can be applied to cloning the Tsps17 gene, as disclosed below.

The sequences of products of the degenerate primer method are identified as potential thermostable DNA polymerase coding sequences if the sequences encode regions of amino acid homology to other known polymerase protein sequences, particularly those of Taq polymerase and Tth polymerase. Portions of the Tsps17 DNA polymerase gene were amplified by the degenerate primer method and then complementary sequences identified in the chromosomal DNA of Thermus species sps17 by Southern blot analysis. The Tsps17 chromosomal DNA was digested with a variety of enzymes and transferred to nitrocellulose filters. Probes labeled with $^{32}P$ or biotin-dUTP were generated for various regions of the gene from the cloned PCR products. The probes were hybridized to the nitrocellulose-bound genomic DNA, allowing identification of the molecular weight of the chromosomal DNA fragment hybridizing to the probe. The use of probes covering the 5' and 3' regions of the gene ensures that DNA fragments identified contain most if not all of the structural gene for the polymerase. Restriction enzymes are identified which can be used to produce fragments that contain the structural gene in a single DNA fragment or in several DNA fragments to facilitate cloning.

Once identified, chromosomal DNA fragments encoding the Tsps17 DNA polymerase gene were cloned. Chromosomal DNA was digested with the identified restriction enzyme, and size fractionated. Fractions containing the desired size range were concentrated, desalted and cloned into cloning vector pBSM13+HindIII::BglII. Clones were identified by hybridization using labeled probes generated from the previously cloned PCR products. The cloned fragments were identified by restriction enzyme and Southern blot analysis.

The DNA sequence and amino acid sequence shown above, and DNA compounds that encode those sequences can be used to design and construct recombinant DNA expression vectors to drive expression of Tsps17 DNA polymerase activity in a wide variety of host cells. A DNA compound encoding all or part of the DNA sequence shown above can also be used as a probe to identify thermostable polymerase-encoding DNA from other organisms, and the amino acid sequence shown above can be used to design peptides for use as immunogens to prepare antibodies that can be used to identify and purify a thermostable polymerase.

The entire coding sequence of the Tsps17 DNA polymerase gene is not required, however, to produce a biologically active gene product with DNA polymerase activity. The availability of DNA encoding the Tsps17 DNA polymerase sequence provides the opportunity to modify the coding sequence so as to generate mutein (mutant protein) forms also having DNA polymerase activity. The amino(N)-terminal portion of the Tsps17 polymerase is not believed to be necessary for activity. Using recombinant DNA methodology, one can delete up to approximately one-third of the N-terminal coding sequence of the Tsps17 gene, clone, and express a gene product that is quite active in polymerase assays. Because certain N-terminal shortened forms of the polymerase are active, the gene constructs used for expression of these polymerases can include the corresponding shortened forms of the coding sequence.

In addition to the N-terminal deletions, individual amino acid residues in the peptide chain of Tsps17 polymerase may be modified by oxidation, reduction, or other derivation, and the protein may be cleaved to obtain fragments that retain activity. Such alterations that do not destroy activity do not remove the protein from the definition of a protein with Tsps17 polymerase activity and so are specifically included within the scope of the present invention.

Modifications to the primary structure of the Tsps17 gene DNA polymerase by deletion, addition, or alteration so as to change the amino acids incorporated into the Tsps17 DNA polymerase during translation can be made without destroying the high temperature DNA polymerase activity of the protein. Such substitutions or other alterations result in the production of proteins having an amino acid sequence encoded by DNA falling within the contemplated scope of the present invention. Likewise, the cloned genomic sequence, or homologous synthetic sequences, of the Tsps17 DNA polymerase gene can be used to express a fusion polypeptide with Tsps17 DNA polymerase activity or to express a protein with an amino acid sequence identical to that of native Tsps17 DNA polymerase. In addition, such expression can be directed by the Tsps17 DNA polymerase gene control sequences or by a control sequence that functions in whatever host is chosen to express the Tsps17 DNA polymerase.

Thus, the present invention provides a coding sequence for Tsps17 DNA polymerase from which expression vectors applicable to a variety of host systems can be constructed and the coding sequence expressed. Portions of the Tsps17 polymerase-encoding sequence are also useful as probes to retrieve other thermostable polymerase-encoding sequences in a variety of species. Accordingly, oligonucleotide probes that encode at least four to six amino acids can be synthesized and used to retrieve additional DNAs encoding a thermostable polymerase. Because there may not be an exact match between the nucleotide sequence of the thermostable DNA polymerase gene of Thermus species sps17 and the corresponding gene of other species, oligomers containing approximately 12-18 nucleotides (encoding the four to six amino sequence) are usually necessary to obtain hybridization under conditions of sufficient stringency to eliminate false positives. Sequences encoding six amino acids supply ample information for such probes.

The present invention, by providing coding sequences and amino acid sequences for Tsps17 DNA polymerase, therefore enables the isolation of other thermostable polymerase enzymes and the coding sequences for those enzymes. The deduced amino acid sequence of the Tsps17 DNA polymerase protein is very similar to the amino acid sequences for other thermostable DNA polymerases, such as those from Taq and Tth (see Ser. No. 455,967, filed Dec. 22, 1989, incorporated herein by reference). These similarities facilitated the identification and isolation of the Tsps17 DNA polymerase coding sequence.

However, regions of dissimilarity between the coding sequences of the three thermostable DNA polymerases can also be used as probes to identify other thermostable polymerase coding sequences which encode enzymes having some properties of one known thermostable polymerase and perhaps different properties. For example, the coding sequence for a thermostable polymerase having some properties of Taq and other divergent properties of Tsps17 may be identified by using probes comprising regions of dissimilarity between Taq and Tsps17.

Whether one desires to produce an enzyme identical to native Tsps17 DNA polymerase or a derivative or homologue of that enzyme, the production of a recombinant form of Tsps17 polymerase typically involves the construction of an expression vector, the transformation of a host cell with the vector, and culture of the transformed host cell under conditions such that expression will occur.

To construct the expression vector, a DNA is obtained that encodes the mature (used here to include all muteins) enzyme or a fusion of the Tsps17 polymerase to an additional sequence that does not destroy activity or to an additional sequence cleavable under controlled conditions (such as treatment with peptidase) to give an active protein. The coding sequence is then placed in operable linkage with suitable control sequences in an expression vector. The vector can be designed to replicate autonomously in the host cell or to integrate into the chromosomal DNA of the host cell. The vector is used to transform a suitable host, and the transformed host is cultured under conditions suitable for expression of recombinant Tsps17 polymerase. The Tsps17 polymerase is isolated from the medium or from the cells, although recovery and purification of the protein may not be necessary in some instances.

Each of the foregoing steps can be done in a variety of ways. For example, the desired coding sequence may be obtained from genomic fragments and used directly in appropriate hosts. The construction of expression vectors operable in a variety of hosts is made using appropriate replicons and control sequences, as set forth generally below. Construction of suitable vectors containing the desired coding and control sequences employs standard ligation and restriction techniques that are well understood in the art. Isolated plasmids, DNA sequences, or synthesized oligonucleotides are cleaved, modified, and religated in the form desired. Suitable restriction sites can, if not normally available, be added to the ends of the coding sequence so as to facilitate construction of an expression vector, as exemplified below.

Site-specific DNA cleavage is performed by treating with the suitable restriction enzyme (or enzymes) under conditions that are generally understood in the art and specified by the manufacturers of commercially available restriction enzymes. See, e.g., New England Biolabs, Product Catalog. In general, about 1 μg of plasmid or other DNA is cleaved by one unit of enzyme in about 20 μl of buffer solution; in the examples below, an excess of restriction enzyme is generally used to ensure complete digestion of the DNA. Incubation times of about one to two hours at about 37° C. are typical, although variations can be tolerated. After each incubation, protein is removed by extraction with phenol and chloroform; this extraction can be followed by ether extraction and recovery of the DNA from aqueous fractions by precipitation with ethanol. If desired, size separation of the cleaved fragments may be performed by polyacrylamide gel or agarose gel electrophoresis using standard techniques. See, e.g., *Methods in Enzymology*, 1980, 65:499–560.

Restriction-cleaved fragments with single-strand "overhanging" termini can be made blunt-ended (double-strand ends) by treating with the large fragment of *E. coli* DNA polymerase I (Klenow) in the presence of the four deoxynucleoside triphosphates (dNTPs) using incubation times of about 15 to 25 minutes at 20° to 25° C. in 50 mM Tris pH 7.6, 50 mM NaCl, 10 mM $MgCl_2$, 10 mM DTT, and 5 to 10 μM dNTPs. The Klenow fragment fills in at 5' protruding ends, but chews back protruding 3' single strands, even though the four dNTPs are present. If desired, selective repair can be performed by supplying only one of the, or selected, dNTPs within the limitations dictated by the nature of the protruding ends. After treatment with Klenow, the mixture is extracted with phenol/chloroform and ethanol precipitated. Similar results can be achieved using S1 nuclease, because treatment under appropriate conditions with S1 nuclease results in hydrolysis of any single-stranded portion of a nucleic acid.

Synthetic oligonucleotides can be prepared using the triester method of Matteucci et al., 1981, *J. Am. Chem. Soc.* 103:3185–3191 or automated synthesis methods. Kinasing of single strands prior to annealing or for labeling is achieved using an excess, e.g., approximately 10 units, of polynucleotide kinase to 0.5 μM substrate in the presence of 50 mM Tris, pH 7.6, 10 mM $MgCl_2$, 5 mM dithiothreitol (DTF), and 1 to 2 μM ATP. If kinasing is for labeling of probe, the ATP will be radioactively labeled with $^{32}P$.

Ligations are performed in 15–30 μl volumes under the following standard conditions and temperatures: 20 mM Tris-Cl, pH 7.5, 10 mM $MgCl_2$, 10 mM DTT, 33 μg/ml BSA, 10 mM-50 mM NaCl, and either 40 μM ATP and 0.01–0.02 (Weiss) units T4 DNA ligase at 20° C. (for ligation of fragments with complementary single-stranded ends) or 1 mM ATP and 0.3–0.6 units T4 DNA ligase at 14° C. (for "blunt end" ligation). Intermolecular ligations of fragments with complementary ends are usually performed at 33–100 μg/ml total DNA concentrations (5–100 nM total ends concentration). Intermolecular blunt end ligations (usually employing a 20–30 fold molar excess of linkers, optionally) are performed at 1 μM total ends concentration.

In vector construction, the vector fragment is commonly treated with bacterial or calf intestinal alkaline phosphatase (BAP or CIAP) to remove the 5' phosphate and prevent religation and reconstruction of the vector. BAP and CIAP digestion conditions are well known in the art, and published protocols usually accompany the commercially available BAP and CIAP enzymes. To recover the nucleic acid fragments, the preparation is extracted with phenol-chloroform and ethanol precipitated to remove AP and purify the DNA. Alternatively, religation of unwanted vector fragments can be prevented by restriction enzyme digestion before or after ligation, if appropriate restriction sites are available.

For portions of vectors or coding sequences that require sequence modifications, a variety of site-specific primer-directed mutagenesis methods are available. The polymerase chain reaction (PCR) can be used to perform site-specific mutagenesis. In another technique now standard in the art, a synthetic oligonucleotide encoding the desired mutation is used as a primer to direct synthesis of a complementary nucleic acid sequence of a single-stranded vector, such as pBS13+, that serves as a template for construction of the extension product of the mutagenizing primer. The mutagenized DNA is transformed into a host bacterium, and cultures of the transformed bacteria are plated and identified. The identification of modified vectors may involve transfer of the DNA of selected transformants to a nitrocellulose filter or other membrane and the "lifts" hybridized with kinased synthetic mutagenic primer at a temperature that permits hybridization of an exact match to the modified sequence but prevents hybridization with the original unmutagenized strand. Transformants that contain DNA that hybridizes with the probe are then cultured (the sequence of the DNA is generally confirmed by sequence analysis) and serve as a reservoir of the modified DNA.

In the construction set forth below, correct ligations for plasmid construction are confirmed by first transforming *E. coli* strain DG101 or another suitable host with the ligation mixture. Successful transformants are selected by ampicillin, tetracycline or other antibiotic resistance or sensitivity or by using other markers, depending on the mode of plasmid construction, as is understood in the art. Plasmids from the transformants are then prepared according to the method of Clewell et al., 1969, *Proc. Natl. Acad. Sci. USA* 62:1159, optionally following chloramphenicol amplification (Clewell, 1972, *J. Bacteriol.* 110:667). Another method for obtaining plasmid DNA is described as the "Base-Acid" extraction method at page 11 of the Bethesda Research Laboratories publication *Focus*, volume 5, number 2, and very pure plasmid DNA can be obtained by replacing steps 12 through 17 of the protocol with CsCl/ethidium bromide ultracentrifugation of the DNA. The isolated DNA is analyzed by restriction enzyme digestion and/or sequenced by the dideoxy method of Sanger et al., 1977, *Proc. Natl. Acad. Sci. USA* 74:5463, as further described by Messing et al., 1981, *Nuc. Acids Res.* 9:309, or by the method of Maxam et al., 1980, *Methods in Enzymology* 65:499.

The control sequences, expression vectors, and transformation methods are dependent on the type of host cell used to express the gene. Generally, procaryotic, yeast, insect, or mammalian cells are used as hosts. Procaryotic hosts are in general the most efficient and convenient for the production of recombinant proteins and are therefore preferred for the expression of Tsps17 polymerase.

The procaryote most frequently used to express recombinant proteins is *E. Coli*. For cloning and sequencing, and for expression of constructions under control of most bacterial promoters, *E. coli* K12 strain MM294, obtained from the *E. coli* Genetic Stock Center under GCSC #6135, can be used as the host. For expression vectors with the $P_L N_{RBS}$ control sequence, *E. coli* K12 strain MC1000 lambda lysogen, $N_7 N_{53} I857$ SusP$_{80}$, ATCC 39531, may be used. *E. coli* DG116, which was deposited with the ATCC (ATCC 53606) on Apr. 7, 1987, and *E. coli* KB2, which was deposited with the ATCC (ATCC 53075) on Mar. 29, 1985, are also useful host cells. For M13 phage recombinants, *E. coli* strains susceptible to phage infection, such as *E. coli* K12 strain DG98, are employed. The DG98 strain was deposited with the ATCC (ATCC 39768) on Jul. 13, 1984.

However, microbial strains other than *E. coli* can also be used, such as bacilli, for example *Bacillus subtilis*, various species of Pseudomonas, and other bacterial strains, for recombinant expression of Tsps17 DNA polymerase. In such procaryotic systems, plasmid vectors that contain replication sites and control sequences derived from the host or a species compatible with the host are typically used.

For example, *E. coli* is typically transformed using derivatives of pBR322, described by Bolivar et al., 1977, *Gene* 2:95. Plasmid pBR322 contains genes for ampicillin and tetracycline resistance. These drug resistance markers can be either retained or destroyed in constructing the desired vector and so help to detect the presence of a desired recombinant. Commonly used procaryotic control sequences, i.e., a promoter for transcription initiation, optionally with an operator, along with a ribosome binding site sequence, include the β-lactamase (penicillinase) and lactose (lac) promoter systems (Chang et al., 1977, *Nature* 198:1056), the tryptophan (trp) promoter system (Goeddel et al., 1980, *Nuc. Acids Res.* 8:4057), and the lambda-derived $P_L$ promoter (Shimatake et al., 1981, *Nature* 292:128) and N-gene ribosome binding site ($N_{RBS}$). A portable control system cassette is set forth in U.S. Pat. No. 4,711,845, issued Dec. 8, 1987. This cassette comprises a $P_L$ promoter operably linked to the $N_{RBS}$ in turn positioned upstream of a third DNA sequence having at least one restriction site that permits cleavage within six bp 3′ of the NRBS sequence. Also useful is the phosphatase A (phoA) system described by Chang et al. in European Patent Publication No. 196,864, published Oct. 8, 1986. However, any available promoter system compatible with procaryotes can be used to construct a Tsps17 expression vector of the invention.

In addition to bacteria, eucaryotic microbes, such as yeast, can also be used as recombinant host cells. Laboratory strains of *Saccharomyces cerevisiae*, Baker's yeast, are most often used, although a number of other strains are commonly available. While vectors employing the two micron origin of replication are common (Broach, 1983, *Meth. Enz.* 101:307), other plasmid vectors suitable for yeast expression are known (see, for example, Stinchcomb et al., 1979, *Nature* 282:39; Tschempe et al., 1980, *Gene* 10:157; and Clarke et al., 1983, *Meth. Enz.* 101:300). Control sequences for yeast vectors include promoters for the synthesis of glycolytic enzymes (Hess et al., 1968, *J. Adv. Enzyme Reg.* 7:149; Holland et al., 1978, *Biotechnology* 17:4900; and Holland et al., 1981, *J. Biol. Chem.* 256:1385). Additional promoters known in the art include the promoter for 3-phosphoglycerate kinase (Hitzeman et al., 1980, *J. Biol. Chem.* 255:2073) and those for other glycolytic enzymes, such as glyceraldehyde 3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other promoters that have the additional advantage of transcription controlled by growth conditions are the promoter regions for alcohol dehydrogenase 2, isocytochrome C, acid phosphatase, degradative enzymes associated with nitrogen metabolism, and enzymes responsible for maltose and galactose utilization (Holland, supra).

Terminator sequences may also be used to enhance expression when placed at the 3′ end of the coding sequence. Such terminators are found in the 3′ untranslated region following the coding sequences in yeast-derived genes. Any vector containing a yeast-compatible promoter, origin of replication, and other control sequences is suitable for use in constructing yeast Tsps17 expression vectors.

The Tsps17 gene can also be expressed in eucaryotic host cell cultures derived from multicellular organisms. See, for example, *Tissue Culture*, Academic Press, Cruz and Patterson, editors (1973). Useful host cell lines include COS-7, COS-A2, CV-1, murine cells such as murine myelomas N51 and VERO, HeLa cells, and Chinese hamster ovary (CHO) cells. Expression vectors for such cells ordinarily include promoters and control sequences compatible with mammalian cells such as, for example, the commonly used early and late promoters from Simian Virus 40 (SV 40) (Fiers et al., 1978, *Nature* 273:113), or other viral promoters such as those derived from polyoma, adenovirus 2, bovine papilloma virus (BPV), or avian sarcoma viruses, or immunoglobulin promoters and heat shock promoters. A system for expressing DNA in mammalian systems using a BPV vector system is disclosed in U.S. Pat. No. 4,419,446. A modification of this system is described in U.S. Pat. No. 4,601,978. General aspects of mammalian cell host system transformations have been described by Axel, U.S. Pat. No. 4,399,216. "Enhancer" regions are also important in optimizing expression; these are, generally, sequences found upstream of the promoter region. Origins of replication may be obtained, if needed, from viral sources. However, integration into the chromosome is a common mechanism for DNA replication in eucaryotes.

Plant cells can also be used as hosts, and control sequences compatible with plant cells, such as the nopaline synthase promoter and polyadenylation signal sequences (Depicker et al., 1982, *J. Mol. Appl. Gen.* 1:561) are available. Expression systems employing insect cells utilizing the control systems provided by baculovirus vectors have also been described (Miller et al., in *Genetic Engineering* (1986), Setlow et al., eds., Plenum Publishing, Vol. 8, pp. 277-297). Insect cell-based expression can be accomplished in *Spodoptera frugipeida*. These systems are also successful in producing recombinant Tsps17 polymerase.

Depending on the host cell used, transformation is done using standard techniques appropriate to such cells. The calcium treatment employing calcium chloride, as described by Cohen, 1972, *Proc. Natl. Acad. Sci. USA* 69:2110 is used for procaryotes or other cells that contain substantial cell wall barriers. Infection with *Agrobacterium tumefaciens* (Shaw et al., 1983, *Gene* 23:315) is used for certain plant cells. For mammalian cells, the calcium phosphate precipitation method of Graham and van der Eb, 1978, *Virology* 52:546 is preferred. Transformations into yeast are carried out according to the method of Van Solingen et al., 1977, *J. Bact.* 130:946 and Hsiao et al., 1979, *Proc. Natl. Acad. Sci. USA* 76:3829.

Once the Tsps17 DNA polymerase has been expressed in a recombinant host cell, purification of the protein may be desired. Although a variety of purification procedures can be used to purify the recombinant thermostable polymerase of the invention, fewer steps may be necessary to yield an enzyme preparation of equal purity. Because *E. coli* host proteins are heat-sensitive, the recombinant thermostable Tsps17 DNA polymerase can be substantially enriched by heat inactivating the crude lysate. This step is done in the presence of a sufficient amount of salt (typically 0.3M ammonium sulfate) to ensure dissociation of the Tsps17 DNA polymerase from the host DNA and to reduce ionic interactions of Tsps17 DNA polymerase with other cell lysate proteins.

In addition, the presence of 0.3M ammonium sulfate promotes hydrophobic interaction with a phenyl sepharose column. Hydrophobic interaction chromatography is a separation technique in which substances are separated on the basis of differing strengths of hydrophobic interaction with an uncharged bed material containing hydrophobic groups. Typically, the column is first equilibrated under conditions favorable to hydrophobic binding, such as high ionic strength. A descending salt gradient may then be used to elute the sample.

According to the invention, an aqueous mixture (containing either native or recombinant Tsps17 DNA polymerase) is loaded onto a column containing a relatively strong hydrophobic gel such as phenyl sepharose (manufactured by Pharmacia) or Phenyl TSK (manufactured by Toyo Soda). To promote hydrophobic interaction with a phenyl sepharose column, a solvent is used which contains, for example, greater than or equal to 0.3M ammonium sulfate. The column and the sample are adjusted to 0.3M ammonium sulfate in 50 mM Tris (pH 7.5) and 0.5 mM EDTA ("TE") buffer that also contains 0.5 mM DTT, and the sample is applied to the column. The column is washed with the 0.3M ammonium sulfate buffer. The enzyme may then be eluted with solvents which attenuate hydrophobic interactions, such as decreasing salt gradients, or increasing gradients or addition of ethylene or propylene glycol, or urea. For native Tsps17 DNA polymerase, a preferred embodiment involves washing the column with a 2M urea in 20% ethylene glycol in TE-DTT wash.

Another purification method which may be used for either recombinant or native Tsps17 DNA polymerase protein is presented below. This method is preferred for the recovery and purification of native protein, and is therefore exemplified by native protein. For recovering the native protein, the cells are grown using any suitable technique. Typically, the Thermus species sps17 cells are grown in a medium of: sodium citrate, 1 mM; potassium phosphate, pH 7.9, 5 mM; ammonium chloride, 10 mM; magnesium sulfate, 0.2 mM; calcium chloride, 0.1 mM; sodium chloride, 1 g/l; yeast extract, 1 g/l; tryptone, 1 g/l; glucose, 2 g/l; and ferrous sulfate, 0.01 mM.

After cell growth, the isolation and purification of the enzyme takes place in six stages, each of which is carried out at a temperature below room temperature, preferably about 0° to about 4° C., unless stated otherwise. In the first stage or step, the cells, if frozen, are thawed, disintegrated by ultrasound, suspended in a buffer at about pH 7.5, and centrifuged.

In the second stage, the supernatant is collected and then fractionated by adding a salt such as dry ammonium sulfate. The appropriate fraction (typically 45-75% of saturation) is collected, dissolved in a 0.2M potassium phosphate buffer preferably at pH 6.5, and dialyzed against the same buffer.

The third step removes nucleic acids and some protein. The fraction from the second stage is applied to a DEAE-cellulose column equilibrated with the same buffer as used above. Then the column is washed with the same buffer and the flow-through protein-containing fractions, determined by absorbance at 280 nm, are collected and dialyzed against a 10 mM potassium phosphate buffer, preferably with the same ingredients as the first buffer, but at a pH 7.5.

In the fourth step, the fraction so collected is applied to a hydroxyapatite column equilibrated with the buffer used for dialysis in the third step. The column is then washed and the enzyme eluted with a linear gradient of a buffer such as 0.01M to 0.5M potassium phosphate buffer at pH 7.5 containing 10 mM 2-mercaptoethanol and 5% glycerine. The pooled fractions containing thermostable DNA polymerase activity are dialyzed against the same buffer used for dialysis in the third step.

In the fifth stage, the dialyzed fraction is applied to a DEAE-cellulose column, equilibrated with the buffer used for dialysis in the third step. The column is then washed and the enzyme eluted with a linear gradient of a buffer such as 0.01 to 0.6M KCl in the buffer used for dialysis in the third step. Fractions with thermostable enzyme activity are then tested for contaminating deoxyribonucleases (endo- and exonucleases) using any suitable procedure. For example, the endonuclease activity may be determined electrophoretically from the change in molecular weight of phage lambda DNA or supercoiled plasmid DNA after incubation with an excess of DNA polymerase. Similarly, exonuclease activity may be determined electrophoretically from the change in molecular weight of restriction enzyme cleaved DNA after treatment with the DNA polymerase fraction. The fractions determined to have polymerase activity but no deoxyribonuclease activity are pooled and dialyzed against the same buffer used in the third step.

In the sixth step, the pooled fractions are placed on a phosphocellulose column with a set bed volume. The column is washed and the enzyme eluted with a linear gradient of a buffer such as 0.01 to 0.4M KCl in a potassium phosphate buffer at pH 7.5. The pooled fractions having thermostable polymerase activity and no deoxyribonuclease activity are dialyzed against a buffer at pH 8.0.

The molecular weight of the DNA polymerase purified from Thermus species sps17 may be determined by any technique, for example, by SDS-PAGE analysis using protein molecular weight markers. The molecular weight of the Tsps17 DNA polymerase I enzyme, calculated from the coding sequence, is about 93,358 daltons. The purification protocol for native Tsps17 DNA polymerase is described in detail in Example 1. As stated and exemplified above, purification of the recombinant Tsps17 polymerase of the invention can be carried out with similar methodology.

For long-term stability, Tsps17 DNA polymerase enzyme can be stored in a buffer that contains one or more non-ionic polymeric detergents. Such detergents are generally those that have a molecular weight in the range of approximately 100 to 250,000 daltons, preferably about 4,000 to 200,000 daltons and stabilize the enzyme at a pH of from about 3.5 to about 9.5, preferably from about 4 to 8.5. Examples of such detergents include those specified on pages 295-298 of McCutcheon's *Emulsifiers & Detergents*, North American edition (1983), published by the McCutcheon Division of MC Publishing Co., 175 Rock Road, Glen Rock, N.J. (USA).

Preferably, the detergents are selected from the group comprising ethoxylated fatty alcohol ethers and lauryl ethers, ethoxylated alkyl phenols, octylphenoxy polyethoxy ethanol compounds, modified oxyethylated and/or oxypropylated straight-chain alcohols, polyethylene glycol monooleate compounds, polysorbate compounds, and phenolic fatty alcohol ethers. More particularly preferred are Tween 20, a polyoxyethylated (20) sorbitan monolaurate from ICI Americas Inc., Wilmington, Del., and Iconol NP-40, an ethoxylated alkyl phenol (nonyl) from BASF Wyandotte Corp. Parsippany, N.J.

The thermostable enzyme of this invention may be used for any purpose in which such enzyme activity is necessary or desired. In a particularly preferred embodiment, the enzyme catalyzes the nucleic acid amplification reaction known as PCR. This process for amplifying nucleic acid sequences is disclosed and claimed in U.S. Pat. No. 4,683,202, issued Jul. 28, 1987, the disclosure of which is incorporated herein by reference. The PCR nucleic acid amplification method involves amplifying at least one specific nucleic acid sequence contained in a nucleic acid or a mixture of nucleic acids and in the most common embodiment, produces double-stranded DNA.

For ease of discussion, the protocol set forth below assumes that the specific sequence to be amplified is contained in a double-stranded nucleic acid. However, the process is equally useful in amplifying single-stranded nucleic acid, such as mRNA, although in the preferred embodiment the ultimate product is still double-stranded DNA. In the amplification of a single-stranded nucleic acid, the first step involves the synthesis of a complementary strand (one of the two amplification primers can be used for this purpose), and the succeeding steps proceed as in the double-stranded amplification process described below.

This amplification process comprises the steps of:
(a) contacting each nucleic acid strand with four different nucleoside triphosphates and one oligonucleotide primer for each strand of the specific sequence being amplified, wherein each primer is selected to be substantially complementary to the different strands of the specific sequence, such that the extension product synthesized from one primer, when it is separated from its complement, can serve as a template for synthesis of the extension product of the other primer, said contacting being at a temperature which allows hybridization of each primer to a complementary nucleic acid strand;
(b) contacting each nucleic acid strand, at the same time as or after step (a), with a DNA polymerase from Thermus species sps17 which enables combination of the nucleoside triphosphates to form primer extension products complementary to each strand of the specific nucleic acid sequence;
(c) maintaining the mixture from step (b) at an effective temperature for an effective time to promote the activity of the enzyme and to synthesize, for each different sequence being amplified, an extension product of each primer which is complementary to each nucleic acid strand template, but not so high as to separate each extension product from the complementary strand template;
(d) heating the mixture from step (c) for an effective time and at an effective temperature to separate the primer extension products from the templates on which they were synthesized to produce single-stranded molecules but not so high as to denature irreversibly the enzyme;
(e) cooling the mixture from step (d) for an effective time and to an effective temperature to promote hybridization of a primer to each of the single-stranded molecules produced in step (d); and
(f) maintaining the mixture from step (e) at an effective temperature for an effective time to promote the activity of the enzyme and to synthesize, for each different sequence being amplified, an extension product of each primer which is complementary to each nucleic acid template produced in step (d) but not so high as to separate each extension product from the complementary strand template. The effective times and temperatures in steps (e) and (f) may coincide, so that steps (e) and (f) can be carried out simultaneously. Steps (d)–(f) are repeated until the desired level of amplification is obtained.

The amplification method is useful not only for producing large amounts of a specific nucleic acid sequence of known sequence but also for producing nucleic acid sequences which are known to exist but are not completely specified. One need know only a sufficient number of bases at both ends of the sequence in sufficient detail so that two oligonucleotide primers can be prepared which will hybridize to different strands of the desired sequence at relative positions along the sequence such that an extension product synthesized from one primer, when separated from the template (complement), can serve as a template for extension of the other primer. The greater the knowledge about the bases at both ends of the sequence, the greater can be the specificity of the primers for the target nucleic acid sequence.

In any case, an initial copy of the sequence to be amplified must be available, although the sequence need not be pure or a discrete molecule. In general, the amplification process involves a chain reaction for producing at least one specific nucleic acid sequence, called the "target" sequence, given that (a) the ends of the target sequence are known in sufficient detail that oligonucleotides can be synthesized which will hybridize to them, and (b) that a small amount of the sequence is available to initiate the chain reaction. The product accumulates exponentially relative to the number of reaction steps involved. The product of the chain reaction is a discrete nucleic acid duplex with termini corresponding to the ends of the specific primers employed.

Any nucleic acid sequence, in purified or nonpurified form, can be utilized as the starting nucleic acid(s), provided it contains or is suspected to contain the specific nucleic acid sequence desired. The nucleic acid to be amplified can be obtained from any source, for example, from plasmids such as pBR322, from cloned DNA or RNA, from natural DNA or RNA from any source, including bacteria, yeast, viruses, organelles, and higher organisms such as plants and animals, or from preparations of nucleic acid made in vitro. DNA or RNA may be extracted from blood, tissue material such as chorionic villi, or amniotic cells by a variety of techniques. See, e.g., Maniatis et al., supra, pp. 280–281. Thus, the process may employ, for example, DNA or RNA, including messenger RNA, which DNA or RNA may be single-stranded or double-stranded. In addition, a DNA-RNA hybrid which contains one strand of each may be utilized. A mixture of any of these nucleic acids can also be employed as can nucleic acids produced from a previous amplification reaction (using the same or different primers). The specific nucleic acid sequence to be amplified may be only a fraction of a large molecule or can be present initially as a discrete molecule, so that the specific sequence constitutes the entire nucleic acid.

The sequence to be amplified need not be present initially in a pure form; the sequence can be a minor fraction of a complex mixture, such as a portion of the β-globin gene contained in whole human DNA (as exemplified in Saiki et al., 1985, *Science* 230:1530–1534) or a portion of a nucleic acid sequence due to a particular microorganism, which organism might constitute only a very minor fraction of a particular biological sample. The cells can be directly used in the amplification process after suspension in hypotonic buffer and heat treatment at about 90°–100° C. until cell lysis and dispersion of intracellular components occur (generally 1 to 15 minutes). After the heating step, the amplification reagents may be added directly to the lysed cells. The starting nucleic acid sequence may contain more than one desired specific nucleic acid sequence. The amplification process is useful not only for producing large amounts of one specific nucleic acid sequence but also for amplifying simultaneously more than one different specific nucleic acid sequence located on the same or different nucleic acid molecules.

Primers play a key role in the PCR process. The word "primer" as used in describing the amplification process can refer to more than one primer, particularly in the case where there is some ambiguity in the information regarding the terminal sequence(s) of the fragment to be amplified. For instance, in the case where a nucleic acid sequence is inferred from protein sequence information, a collection of primers containing sequences representing all possible codon variations based on degeneracy of the genetic code will be used for each strand. One primer from this collection will be sufficiently homologous with the end of the desired sequence to be amplified to be useful for amplification.

In addition, more than one specific nucleic acid sequence can be amplified from the first nucleic acid or mixture of nucleic acids, so long as the appropriate number of different oligonucleotide primers are utilized. For example, if two different specific nucleic acid sequences are to be produced, four primers are utilized. Two of the primers are specific for one of the specific nucleic acid sequences and the other two primers are specific for the second specific nucleic acid sequence. In this manner, each of the two different specific sequences can be produced exponentially by the present process. When allelic variants or different members of a multigene family are to be amplified, however, one can often amplify several different sequences with a single set of primers.

A sequence within a given sequence can be amplified after a given number of amplifications to obtain greater specificity of the reaction by adding after at least one cycle of amplification a set of primers that are complementary to internal sequences (that are not on the ends) of the sequence to be amplified. Such primers may be added at any stage and will provide a shorter amplified fragment. Alternatively, a longer fragment can be prepared by using primers with non-complementary 5' ends but having some 3' overlap with the 5' ends of the primers previously utilized in the amplification.

Primers also play a key role when the amplification process is used for in vitro mutagenesis. The product of an amplification reaction where the primers employed are not exactly complementary to the original template will contain the sequence of the primer rather than the template, so introducing an in vitro mutation. Although the initial cycles may be somewhat inefficient, due to the mismatch between the mutagenic primer and the target, in further cycles the mutation will be amplified with an undiminished efficiency because no further mispaired priming is required. The process of making an altered DNA sequence as described above could be repeated on the altered DNA using different primers to induce further sequence changes. In this way, a series of mutated sequences can gradually be produced wherein each new addition to the series differs from the last in a minor way, but from the original DNA source sequence in an increasingly major way.

Because the primer can contain as part of its sequence a non-complementary sequence, provided that a sufficient amount of the primer contains a sequence that is complementary to the strand to be amplified, many other advantages can be realized. For example, a nucleotide sequence that is not complementary to the template sequence (such as, e.g., a promoter, linker, coding sequence, etc.) may be attached at the 5' end of one or both of the primers and so appended to the product of the amplification process. After the extension primer is added, sufficient cycles are run to achieve the desired amount of new template containing the non-complementary nucleotide insert. This allows production of large quantities of the combined fragments in a relatively short period of time (e.g., two hours or less) using a simple technique.

Oligonucleotide primers can be prepared using any suitable method, such as, for example, the phosphotriester and phosphodiester methods described above, or automated embodiments thereof. In one such automated embodiment, diethylphosphoramidites are used as starting materials and may be synthesized as described by Beaucage et al., 1981, *Tetrahedron Letters* 22:1859–1862. One method for synthesizing oligonucleotides on a modified solid support is described in U.S. Pat. No. 4,458,066. One can also use a primer that has been isolated from a biological source (such as a restriction endonuclease digest).

No matter what primers are used, however, the reaction mixture must contain a template for PCR to occur, because the specific nucleic acid sequence is produced by using a nucleic acid containing that sequence as a template. The first step involves contacting each nucleic acid strand with four different nucleoside triphosphates and one oligonucleotide primer for each strand of each specific nucleic acid sequence being amplified or detected. If the nucleic acids to be amplified or detected are DNA, then the nucleoside triphosphates are usually dATP, dCTP, dGTP, and dTTP, although various nucleotide derivatives can also be used in the process. The concentration of nucleotide triphosphates can vary widely. Typically the concentration is 50–200 $\mu$M in each dNTP in the buffer for amplification, and MgCl$_2$ is present in the buffer in an amount of 1 to 3 mM to activate the polymerase and increase the specificity of the reaction. However, dNTP concentrations of 1–20 $\mu$M may be preferred for some applications, such as DNA sequencing.

The nucleic acid strands of the target nucleic acid serve as templates for the synthesis of additional nucleic acid strands, which are extension products of the primers. This synthesis can be performed using any suitable method, but generally occurs in a buffered aqueous solution, preferably at a pH of 7 to 9, most preferably about 8. To facilitate synthesis, a molar excess of the two oligonucleotide primers is added to the buffer containing the template strands. As a practical matter, the amount of primer added will generally be in molar excess over the amount of complementary strand (template) when the sequence to be amplified is contained in a mixture of complicated long-chain nucleic acid strands. A large molar excess is preferred to improve the efficiency of the process. Accordingly, primer:template ratios of about 1000:1 are generally employed for cloned DNA templates, and primer:template ratios of about $10^8$:1 are generally employed for amplification from complex genomic samples.

The mixture of template, primers, and nucleoside triphosphates is then treated according to whether the nucleic acids being amplified or detected are double- or single-stranded. If the nucleic acids are single-stranded, then no denaturation step need be employed, and the reaction mixture is held at a temperature which promotes hybridization of the primer to its complementary target (template) sequence. Such temperature is generally from about 35° C. to 65° C. or more, preferably about 37°–60° C. for an effective time, generally from a few seconds to five minutes, preferably from 30 seconds to one minute. A hybridization temperature of 35° C.–80° C. may be used for Tsps17 DNA polymerase, and 15-mer or longer primers are used to increase the specificity of primer hybridization. Shorter primers require lower hybridization temperatures or agents which stabilize double-stranded DNA.

The complement to the original single-stranded nucleic acids can be synthesized by adding Tsps17 DNA polymerase in the presence of the appropriate buffer, dNTPs, and one or more oligonucleotide primers. If an appropriate single primer is added, the primer extension product will be complementary to the single-stranded nucleic acid and will be hybridized with the nucleic acid strand in a duplex of strands of equal or unequal length (depending where the primer hybridizes on the template), which may then be separated into single strands as described above to produce two single, separated, complementary strands. Alternatively, two or more appropriate primers (one of which will prime synthesis using the extension product of the other primer as a template) may be added to the single-stranded nucleic acid and the reaction carried out.

If the nucleic acid contains two strands, as in the case of amplification of a double-stranded target or second-cycle amplification of a single-stranded target, the strands of nucleic acid must be separated before the primers are hybridized. This strand separation can be accomplished by any suitable denaturing method, including physical, chemical or enzymatic means. One preferred physical method of separating the strands of the nucleic acid involves heating the nucleic acid until complete (>99%) denaturation occurs. Typical heat denaturation involves temperatures ranging from about 90° C. to 105° C. for times generally ranging from about a few seconds to 4 minutes, depending on the composition and size of the nucleic acid. Preferably, the effective denaturing temperature is 90° C.–100° C. for a few seconds to 1 minute. Strand separation may also be induced by an enzyme from the class of enzymes known as helicases or the enzyme RecA, which has helicase activity and in the presence of riboATP is known to denature DNA. The reaction conditions suitable for separating the strands of nucleic acids with helicases are described by Kuhn Hoffmann-Berling, 1978, *CSH-Quantitative Biology* 43:63, and techniques for using RecA are reviewed in Radding, 1982, *Ann. Rev. Genetics* 16:405–437. The denaturation produces two separated complementary strands of equal or unequal length.

If the double-stranded nucleic acid is denatured by heat, the reaction mixture is allowed to cool to a temperature which promotes hybridization of each primer to the complementary target (template) sequence. This temperature is usually from about 35° C. to 65° C. or more, depending on reagents, preferably 37° C.–60° C. The hybridization temperature is maintained for an effective time, generally 30 seconds to 5 minutes, and preferably 1–3 minutes. In practical terms, the temperature is simply lowered from about 95° C. to as low as 37° C., and hybridization occurs at a temperature within this range.

Whether the nucleic acid is single- or double-stranded, the DNA polymerase from Thermus species sps17 may be added at the denaturation step or when the temperature is being reduced to or is in the range for promoting hybridization. Although the thermostability of Tsps17 polymerase allows one to add Tsps17 polymerase to the reaction mixture at any time, one can substantially inhibit non-specific amplification by adding the polymerase to the reaction mixture at a point in time when the mixture will not be cooled below the stringent hybridization temperature. After hybridization, the reaction mixture is then heated to or maintained at a temperature at which the activity of the enzyme is promoted or optimized, i.e., a temperature sufficient to increase the activity of the enzyme in facilitating synthesis of the primer extension products from the hybridized primer and template. The temperature must actually be sufficient to synthesize an extension product of each primer which is complementary to each nucleic acid template, but must not be so high as to denature each extension product from its complementary template (i.e., the temperature is generally less than about 80° C.–90° C).

Depending on the nucleic acid(s) employed, the typical temperature effective for this synthesis reaction generally ranges from about 40° to 80° C., preferably 50°–75° C. The temperature more preferably ranges from about 65°–75° C. for Thermus species sps17 DNA polymerase. The period of time required for this synthesis may range from several seconds to 40 minutes or more, depending mainly on the temperature, the length of the nucleic acid, the enzyme, and the complexity of the nucleic acid mixture. The extension time is usually about 30 seconds to three minutes. If the nucleic acid is longer, a longer time period is generally required for complementary strand synthesis. The newly synthesized strand and the complement nucleic acid strand form a double-stranded molecule which is used in the succeeding steps of the amplification process.

In the next step, the strands of the double-stranded molecule are separated by heat denaturation at a temperature and for a time effective to denature the molecule, but not at a temperature and for a period so long that the thermostable enzyme is completely and irreversibly denatured or inactivated. After this denaturation of template, the temperature is decreased to a level which promotes hybridization of the primer to the complementary single-stranded molecule (template) produced from the previous step, as described above.

After this hybridization step, or concurrently with the hybridization step, the temperature is adjusted to a temperature that is effective to promote the activity of the thermostable enzyme to enable synthesis of a primer extension product using as a template both the newly synthesized and the original strands. The temperature again must not be so high as to separate (denature) the extension product from its template, as described above. Hybridization may occur during this step, so that the previous step of cooling after denaturation is not required. In such a case, using simultaneous steps, the preferred temperature range is 50°–70° C.

The heating and cooling steps involved in one cycle of strand separation, hybridization, and extension product synthesis can be repeated as often as needed to produce the desired quantity of the specific nucleic acid sequence. The only limitation is the amount of the primers, thermostable enzyme, and nucleoside triphosphates present. Usually, from 15 to 30 cycles are completed. For diagnostic detection of amplified DNA, the number of cycles will depend on the nature of the sample and the sensitivity of the detection process used after amplification. If the sample is a complex mixture of nucleic acids, more cycles will usually be required to amplify the signal sufficiently for detection. For general amplification and detection, the process is usually repeated about 15 times. When amplification is used to generate sequences to be detected with labeled sequence-specific probes and when human genomic DNA is the target of amplification, the process is usually repeated 15 to 30 times to amplify the sequence sufficiently that a clearly detectable signal is produced, i.e., so that background noise does not interfere with detection.

No additional nucleotides, primers, or thermostable enzyme need be added after the initial addition, provided that no key reagent has been exhausted and that the enzyme has not become denatured or irreversibly inactivated, in which case additional polymerase or other reagent would have to be added for the reaction to continue. Addition of such materials at each step, however, will not adversely affect the reaction. After the appropriate number of cycles has been completed to produce the desired amount of the specific nucleic acid sequence, the reaction may be halted in the usual manner, e.g., by inactivating the enzyme by adding EDTA, phenol, SDS, or $CHCl_3$ or by separating the components of the reaction.

The amplification process may be conducted continuously. In one embodiment of an automated process, the reaction mixture may be temperature cycled such that the temperature is programmed to be controlled at a certain level for a certain time. One such instrument for this purpose is the automated machine for handling the amplification reaction manufactured and developed by Hoffmann-La Roche Inc. and marketed through Perkin Elmer (Norwalk, Conn.). Detailed instructions for carrying out PCR with the instrument are available upon purchase of the instrument.

Tsps17 DNA polymerase is very useful in the diverse processes in which amplification of a nucleic acid sequence by the polymerase chain reaction is useful. The amplification method may be utilized to clone a particular nucleic acid sequence for insertion into a suitable expression vector, as described in U.S. Pat. No. 4,800,159. The vector may be used to transform an appropriate host organism to produce the gene product of the sequence by standard methods of recombinant DNA technology. Such cloning may involve direct ligation into a vector using blunt-end ligation, or use of restriction enzymes to cleave at sites contained within the primers or amplified target sequence. Other processes suitable for Tsps17 polymerase include those described in U.S. Pat. Nos. 4,683,194; 4,683,195; and 4,683,202 and European Patent Publication Nos. 229,701; 237,362; and 258,017; these patents and publications are incorporated herein by reference. In addition, the present enzyme is useful in asymmetric PCR (see Gyllensten and Erlich, 1988, *Proc. Natl. Acad. Sci. USA* 85:7652–7656, incorporated herein by reference); inverse PCR (Ochman et al., 1988, *Genetics* 120:621, incorporated herein by reference); and for DNA sequencing (see Innis et al., 1988, *Proc. Natl. Acad. Sci. USA* 85:9436–9440, and McConlogue et al., 1988, *Nuc. Acids Res.* 16(20):9869). Tsps17 polymerase is also believed to have reverse transcriptase activity, (see copending Ser. No. 455,611, filed Dec. 22, 1989, incorporated herein by reference), and 5'→3' exonuclease activity (also known as structure dependent single strand endonuclease (SDSSE) activity).

The reverse transcriptase activity of the Tsps17 DNA polymerase permits this enzyme to be used in methods for transcribing and amplifying RNA. The improvement of such methods resides in the use of a single enzyme, whereas previous methods have required more than one enzyme. Such methods are described in detail in Ser. No. 455,611, filed Dec. 22, 1989, and in the continuation-in-part of that application, Ser. No. 585,471, filed Sep. 20, 1990, both of which are incorporated herein by reference.

In the amplification of an RNA molecule by Tsps17 DNA polymerase, the first extension reaction is reverse transcription, and a DNA strand is produced from an RNA/cDNA hybrid molecule. The second extension reaction, using the DNA strand as a template, produces a double-stranded DNA molecule. Thus, synthesis of a complementary DNA strand from an RNA template with Tsps17 DNA polymerase provides the starting material for amplification by PCR.

When Tsps17 DNA polymerase is used for nucleic acid transcription from an RNA template, it has been found that the use of buffers which contain $Mn^{2+}$ provide improved stimulation of Tsps17 reverse transcriptase activity compared to previously used, $Mg^{2+}$-containing reverse transcription buffers. Consequently, increased cDNA yields also result from these methods.

As stated above, the product of RNA transcription by Tsps17 DNA polymerase is an RNA/cDNA hybrid molecule. The RNA is then removed by heat denaturation or any number of other known methods including alkali, heat or enzyme treatment. The remaining cDNA strand then serves as a template for polymerization of a self-complementary strand, thereby providing a double-stranded cDNA molecule suitable for amplification or other manipulation. The second strand synthesis requires a sequence specific primer and Tsps17 DNA polymerase.

The SDSSE activity of Tsps17 may limit the amount of product produced by PCR and create a plateau phenomenon in the normally exponential accumulation of product. The SDSSE activity may also limit the size of the PCR product produced or limit the ability to generate PCR product from GC-rich target template. The SDSSE activity can also be important in assays such as those described in Ser. No. 563,758, filed Aug. 6, 1990, incorporated herein by reference. SDSSE activity relates to the hydrolysis of phosphodiester bonds. SDSSE activity generally excises 5' terminal regions of double-stranded DNA, thereby releasing 5'-mono-and oligonucleotides. The preferred substrate for the SDSSE activity is displaced single-stranded DNA, with hydrolysis of the phosphodiester bond which occurs between the displaced single-stranded DNA and the double-helical DNA. The preferred cleavage site is a phosphodiester bond in the double helical region.

Site-directed mutagenesis or deletion mutagenesis can be utilized to eliminate the SDSSE activity of a polymerase having such activity. Such polymerases are an important aspect of the present invention. For example, a deletion of the first 76 amino acids, creating a protein beginning with Ala 77, is believed to be effective for reducing the SDSSE activity of *Thermus aquaticus* DNA polymerase. Those of skill in the art recognize that when such a deletion mutant is to be expressed in recombinant host cells, a methionine codon is usually placed at the 5' end of the coding sequence, so that the amino terminal sequence of the deletion mutant protein would be MET-ALA. Alanine 77 is found within the sequence HEAYG in Taq DNA polymerase. A similar sequence motif HEAYE is found in Tth and Thermus species Z05 and sps17 DNA polymerases. For Tsps17 DNA polymerase, the corresponding alanine in this motif is Ala 74. A deletion up to the alanine in the motif HEAY(G/E) in any thermostable DNA polymerase containing this sequence can reduce or eliminate the SDSSE activity.

Furthermore, a site-directed mutation of G to A in the second position of the codon for Gly at residue 46 in the Taq DNA polymerase sequence has been found to result in an approximately 100-fold reduction of SDSSE activity with no apparent change in polymerase activity, processivity or extension rate. This site-directed mutation of the Taq DNA polymerase nucleotide sequence results in an amino acid change of Gly (46) to Asp. Glycine 46 is conserved in Thermus species sps17 DNA polymerase, but is located at residue 43, and the same Gly to Asp mutation would have a similar effect on Tsps17 SDSSE activity.

Tsps17 Gly 43 is found in a conserved AVYGF sequence domain, and changing the glycine to aspartic acid within this conserved sequence domain of any polymerase is also expected to alter SDSSE activity. In addition, a deletion of all amino terminal amino acids up to and including the glycine in the AVYGF domain will also alter the SDSSE activity of any thermostable DNA polymerase having this sequence domain, including the DNA polymerase of Thermus species sps17.

The following examples are offered by way of illustration only and are by no means intended to limit the scope of the claimed invention. In these examples, all percentages are by weight if for solids and by volume if for liquids, unless otherwise noted, and all temperatures are given in degrees Celsius.

EXAMPLE 1

Purification of Thermus Species sps17 DNA Polymerase

This example describes the isolation of Tsps17 DNA polymerase from Thermus species sps17.

Thermus species sps17 cells are grown in flasks in the following medium, adjusted to pH 8.0 with ammonium hydroxide: sodium citrate, 1 mM; potassium phosphate, pH 7.9, 5 mM; ammonium chloride, 10 mM; magnesium sulfate, 0.2 mM; calcium chloride, 0.1 mM; sodium chloride, 1 g/l; yeast extract, 1 g/l; tryptone, 1 g/l; glucose, 2 g/l; and ferrous sulfate, 0.01 mM.

The cells are cultured overnight at 70° C., and 600 ml from the flask is used to inoculate 10 liters of the same medium in a fermentor. The fermentor operates with dissolved oxygen at 40%, a temperature of 70° C. and a stirring rate of 400 rpm.

The above culture of the Thermus species sps17 cells is harvested by centrifugation after nine hours of cultivation, in late log phase, at a cell density of 1.4 g dry weight/l. Twenty grams of cells are resuspended in 80 ml of a buffer consisting of 50 mM Tris HCl pH 7.5, 0.1 mM EDTA. The cells are lysed and the lysate is centrifuged for two hours at 35,000 rpm in a Beckman TI 45 rotor at 4° C. The supernatant is collected (fraction A) and the protein fraction precipitating between 45 and 75% saturation of ammonium sulfate is collected, dissolved in a buffer consisting of 0.2M potassium phosphate buffer, pH 6.5, 10 mM 2-mercaptoethanol, and 5% glycerine, and finally dialyzed against the same buffer to yield fraction B.

Fraction B is applied to a 2.2×30 cm column of DEAE-cellulose, equilibrated with the above described buffer. The column is then washed with the same buffer and the fractions containing protein (determined by absorbance at 280 nM) are collected. The combined protein fraction is dialyzed against a second buffer, containing 0.01M potassium phosphate buffer, pH 7.5, 10 mM 2-mercaptoethanol, and 5% glycerine, to yield fraction C.

Fraction C is applied to a 2.6×21 cm column of hydroxyapatite, equilibrated with a second buffer. The column is then washed and the enzyme is eluted with a linear gradient of 0.01–0.5M potassium phosphate buffer, pH 7.5, containing 10 mM 2-mercaptoethanol and 5% glycerine. Fractions containing DNA polymerase activity (90–180 mM potassium phosphate) are combined, concentrated four-fold using an Amicon stirred cell and YM10 membrane, and dialyzed against the second buffer to yield fraction D.

Fraction D is applied to a 1.6×28 cm column of DEAE-cellulose, equilibrated with the second buffer. The column is washed and the polymerase is eluted with a linear gradient of 0.01–0.5M potassium phosphate in the second buffer. The fractions are assayed for contaminating endonuclease(s) and exonuclease(s) by electrophoretically detecting the change in molecular weight of phage lambda DNA or supercoiled plasmid DNA after incubation with an excess of DNA polymerase (for endonuclease) and after treatment with a restriction enzyme that cleaves the DNA into several fragments (for exonuclease). Only those DNA polymerase fractions (65–95 mM potassium phosphate) having minimal nuclease contamination are pooled. To the pool is added autoclaved gelatin in an amount of 250 g/ml, and dialysis is conducted against the second buffer to yield Fraction E.

Fraction E is applied to a phosphocellulose column and eluted with a 100 ml gradient (0.01–0.4M KCl gradient in 20 mM potassium phosphate buffer pH 7.5). The fractions are assayed for contaminating endo/exonuclease(s) as described above as well as for polymerase activity (by the method of Kaledin et al.) and then pooled. The pooled fractions are dialyzed against the second buffer, and then concentrated by dialysis against 50% glycerine and the second buffer to yield the desired polymerase.

EXAMPLE 2

Isolation of DNA Fragments Encoding Tsps17 DNA Polymerase

This Example presents a degenerate primer method used to isolate DNA fragments that encode Tsps17 DNA polymerase. In this method, various sets of forward and reverse primers were used in the polymerase chain reaction. These primers were designed to various motifs in the template binding domains of thermostable DNA polymerases.

Two methods were used to determine which degenerate primer sets produced correct regions of the Tsps17 polymerase gene. The products were identified as correct either by DNA sequence analysis or by restriction enzyme analysis. The product was considered analogous to the Taq product when several restriction sites present in the Taq DNA polymerase gene were also present in the Tsps17 product. In addition, the product was identified as distinct from the Taq product when restriction sites present in the Taq product were absent in the Tsps17 product and when restriction sites absent in the Taq product were present in the Tsps17 product. The degenerate primer sets which produced correct regions of the Tsps17 polymerase gene are listed below in Table 1.

In Table 1, A is Adenine; C is Cytidine; G is Guanidine; T is Thymine; Y is C+T (pYrimidine); S is G+C (Strong interaction; three hydrogen bonds); W is A+T (Weak interaction; two hydrogen bonds); N is A+C+G+T (aNy); and R is G+A (puRine). In the examples below, where a forward or a reverse primer is indicated as "DGXX-DGXX" or "DGXX/DGXX," one should assume that all of the primers between the two XX numbers shown were used as the forward or reverse primer. All of the primer sets discussed below are shown in the table.

From the table, one should note that all of the primers encode a restriction site at the 5' end of the primer to facilitate cloning and that the amino acid sequences shown for the reverse primers are encoded by a sequence complementary to the primer.

TABLE 1

| Degenerate Primer Sets That Produced Correct Regions of sps17 Polymerase Gene | | | |
|---|---|---|---|
| Forward Primer | Sequence | Reverse Primer | Sequence |
| DG157 (Seq ID No. 3) | GlnAsnIleProVal 5'CGAGATCTCARAAYATHCCSGT | DG169 (Seq ID No. 13) | 5'CGGAATTCGTYTCNACRTASCC ThrGluValTyrGly |
| DG157 (Seq ID No. 3) | GlnAsnIleProVal 5'CGAGATCTCARAAYATHCCSGT | DG174 (Seq ID No. 14) | 5'CGGAATTCATRCGYTCSGC MetArgGluAla |
| MK143 (Seq ID No. 4) | AlaValLeuAlaHisMet 5'CCGCTGTCCTGGCCCACATG | MK131 (Seq ID No. 15) | 5'CCCGGATCAGGTTCTCGTC ArgIleLeuAsnGluAsp |
| DG140 - DG141 (Seq ID No. 5) | AlaHisMetGluAla 5'CGAGATCTGCNCAYATGGAAGC | MK131 (Seq ID No. 15) | 5'CCCGGATCAGGTTCTCGTC ArgIleLeuAsnGluAsp |
| (Seq ID No. 6) | AlaHisMetGluAla 5'CGAGATCTGCNCAYATGGAGGC | | |
| DG124 - DG125 (Seq ID No. 7) | GluProMetTrpAla 5'CGAGATCTGARCCWATGTGGGC | DG130 - DG131 (Seq ID No. 16) | 5'CGGAATTCATNGGRTCRTCWCC MetProAspAspGly |
| (Seq ID No. 8) | GluProMetTrpAla 5'CGAGATCTGARCCSATGTGGGC | (Seq ID No. 17) | 5'CGGAATTCATNGGRTCRTCSCC MetProAspAspGly |
| DG100 - DG101 (Seq ID No. 9) | GlyGluLysThrAla 5'CGAGATCTGGNGARAARACSGC | DG130 - DG131 (Seq ID No. 16) | 5'CGGAATTCATNGGRTCRTCWCC MetProAspAspGly |
| (Seq ID No. 10) | GlyGluLysThrAla 5'CGAGATCTGGNGARAARACWGC | (Seq ID No. 17) | 5'CGGAATTCATNGGRTCRTCSCC MetProAspAspGly |
| DG152 - DG153 (Seq ID No. 11) | GluAlaAspAspVal 5'CGAGATCTGARGCNGAYGATGT | DG148 - DG149 (Seq ID No. 18) | 5'CGGAATTCGCNGTYTTYTCWCC AlaThrLysGluGly |
| (Seq ID No. 12) | GluAlaAspAspVal 5'CGAGATCTGARGCNGAYGACGT | (Seq ID No. 19) | 5'CGGAATTCGCNGTYTTYTCSCC AlaThrLysGluGly |
| DG150 - DG151 (SEQ ID No. 20) | ValPheAspAlaAsnLys 5'CGAGATCTGTNTTYGAYGCWAA | DG148 - DG149 (SEQ ID No. 18) | 5'CGGAATTCGCNGTYTTYTCWCC AlaThrLysGluGly |
| (SEQ ID No. 21) | ValPheAspAlaAsnLys 5'CGAGATCTGTNTTYGAYGCSAA | (SEQ ID No. 19) | 5'CGGAATTCGCNGTYTTYTCSCC AlaThrLysGluGly |
| DG164 - DG167 (SEQ ID No. 22) | GlyTyrValGluThr 5'CGAGATCTGGNTAYGTWGAAAC | DG181 - DG182 (SEQ ID No. 28) | 5'CGGAATTCNGCNGCNGTSCCYTG AspAlaAlaThrGlyGln Glu |
| (SEQ ID No. 23) | GlyTyrValGluThr 5'CGAGATCTGGNTAYGTWGAGAC | (SEQ ID No. 29) | 5'CGGAATTCNGCNGCNGTWCCYTG AspAlaAlaThrGlyGln |

TABLE 1-continued

Degenerate Primer Sets That Produced Correct Regions of sps17 Polymerase Gene

| Forward Primer | Sequence | Reverse Primer | Sequence |
|---|---|---|---|
| (SEQ ID No. 24) | GlyTyrValGluThr<br>5'CGAGATCTGGNTAYGTSGAAAC | | Glu |
| (SEQ ID No. 25) | GlyTyrValGluThr<br>5'CGAGATCTGGNTAYGTSGAGAC | | |
| DG164 - DG167<br>(SEQ ID No. 22) | GlyTyrValGluThr<br>5'CGAGATCTGGNTAYGTWGAAAC | DG160 - DG163<br>(SEQ ID No. 30) | 5'CGGAATTCRTCRTGWACCTG<br>GluAspHisValGln<br>Asp |
| (SEQ ID No. 23) | GlyTyrValGluThr<br>5'CGAGATCTGGNTAYGTWGAGAC | (SEQ ID No. 31) | 5'CGGAATTCRTCRTGWACTTG<br>GluAspHisValGln<br>Asp |
| (SEQ ID No. 24) | GlyTyrValGluThr<br>5'CGAGATCTGGNTAYGTSGAAAC | (SEQ ID No. 32) | 5'CGGAATTCRTCRTGSACCTG<br>GluAspHisValGln<br>Asp |
| (SEQ ID No. 25) | GlyTyrValGluThr<br>5'CGAGATCTGGNTAYGTSGAGAC | (SEQ ID No. 33) | 5'CGGAATTCRTCRTGSACTTG<br>GluAspHisValGln<br>Asp |
| DG152 - DG153<br>(SEQ ID No. 26) | GluAlaAspAspVal<br>5'CGAGATCTGARGCNGAYGATGT | DG126 - DG127<br>(SEQ ID No. 34) | 5'CGGAATTCGCCCACATWGGYTC<br>AlaTrpMetProGlu |
| (SEQ ID No. 27) | GluAlaAspAspVal<br>5'CGAGATCTGARGCNGAYGACGT | (SEQ ID No. 35) | 5'CGGAATTCGCCCACATSGGYTC<br>AlaTrpMetProGlu |

When the above degenerate primer sets were used in the PCR to amplify regions of the Tsps17 polymerase gene, the following reaction conditions were used:

10 mM Tris, pH 8.3; 50 mM KCl; 1.5 mM $MgCl_2$; gelatin; 200 μM each dNTP; 10 ng chromosomal DNA, $4.7 \times 10^6$ base pairs equivalent to $5.15 \times 10^{-18}$ g/chromosome or $3.2 \times 10^{-4}$M; 500 nM each oligo primer set; and 2.5–5 units Taq polymerase.

The temperature cycle for the PCR was 5 cycles of 1.5 minutes at 45° C., a 2 minute ramp to 98° C. and 45 seconds at 98° C., followed by 30 cycles of 50° C. for 2 minutes, a step to the denaturation temperature of 98° C., and 45 seconds at 98° C. The PCR products generated were then chloroform extracted to remove oil, desalted over a biogel P-4 spin column, and restricted with the indicated restfiction enzyme according to the manufacturer's specifications.

The PCR products were analyzed on 10% polyacrylamide gels using MspI-digested pBR322 as molecular weight standard. Undigested PCR products were also included on the gel analysis to indicate contaminating PCR products which might confuse the digestion analysis. In some instances, the restriction analysis was performed on reamplification of gel purified PCR products.

Listed below are the results for the various degenerate primer sets that produced correct regions of the Tsps17 polymerase gene (see Tables 1A–1J). The numbers in each table below represent the size, in base pairs, determined from the confirmed sequence ("expected") or experimental data ("experimental").

TABLE 1A

Primer Set DG157/DG169 (Seq ID No. 3/Seq ID No. 13)

To obtain the results in this table, chromosomal DNA was amplified with the listed primer set, and the PCR product was directly analyzed by restriction analysis.

| | Taq | | sps17 | |
|---|---|---|---|---|
| Enzyme | Expected | Experimental | Expected | Experimental |
| Undigested | 438 | 440 | 438 | 440 |
| StuI | 336 | 330 | 387 | 380 |
| | 102 | 107 | 51 | 50 |
| SmaI | 222 | 229 | 438 | 440 |
| | 216 | 215 | | |
| SacI | 328 | 310 | 198 | 208 |
| | 110 | 127 | 133 | 138 |
| | | | 107 | 117 |

TABLE 1B

Primer Set MK143/MK131

To obtain the results in this table, chromosomal DNA was amplified with the listed primer set, and the PCR product was directly analyzed by restriction analysis.

| | Taq | | sps17 | |
|---|---|---|---|---|
| Enzyme | Expected | Experimental | Expected | Experimental |
| Undigested | 579 | 580 | 580 | 580 |
| SacI | 299 | 335 | 234 | 252 |
| | 234 | 280 | 176 | 195 |
| | 46 | 58 | 69 | 82 |
| | | | 51 | 59 |
| | | | 49 | 54 |
| BamHI | 468 | 450 | 300 | 305 |
| | 111 | 128 | 279 | 280 |
| PstI | 292 | 298 | 428 | 450 |
| | 287 | 284 | 151 | 175 |

TABLE 1C

Primer Set DG140–DG141 (Seq ID Nos. 5 and 6)/MK131 (Seq ID No. 15)

The results in this Table were obtained from an analysis which consisted of two series of PCR. First, chromosomal DNA was amplified with an external set of primers (DG136–DG137 [Seq ID Nos. 39 and 40] and DG168–DG169 [Seq ID Nos. 41 and 13]), from which no visible product was detectable. Then, 0.1 μl and 1 μl equivalents of the above reaction product was reamplified directly with the primer combination DG140–DG141 (Seq ID Nos. 5 and 6) and MK131 (Seq ID No. 15), and the product thereof was analyzed directly by restriction enzyme digestion.

DG136–Seq ID No. 39          DG137–Seq ID No. 40

TABLE 1C-continued

Primer Set DG140–DG141 (Seq ID Nos. 5 and 6)/MK131 (Seq ID No. 15)

```
           GluGlyGluGlu              GluGlyGluGlu
                    Asp                       Asp
     CGAGATCTGARGGWGARGA    CGAGATCTGARGGSGARGA
           DG168-Seq ID No. 41
     CGGAATTCGTYTCNACRTAWCC
              ThrGluValTyrGly
```

The second PCR series was carried out identically. Chromosomal DNA as amplified with the external primer set, DG136–DG137 (Seq ID Nos. 39 and 40) and DG168–DG169 (Seq ID Nos. 41 and 13), for which no product was detectable. Then, 1/100 to 1/1000 of that PCR product was reamplified with the internal primer set, DG140–DG141 (Seq ID Nos. 5 and 6) to MK131 (Seq ID No. 15). The product of this second PCR was analyzed by restriction digest. Although the restriction analysis was complicated by the presence of partially digested product, many of the expected bands were evident.

| Enzyme | Taq Expected | Taq Experimental | sps17 Expected | sps17 Experimental |
|---|---|---|---|---|
| Undigested | 576 | 520 | 576 | 520 |
| SacI | 296 | 297 | | |
| | 234 | 245 | 234 | 245 |
| | 46 | 55 | 173 | 125 |
| | | | 69 | 99 |
| | | | 51 | 80 |
| | | | 49 | 60 |
| | | | | 54 |
| BamHI | 465 | 435 | 300 | 400 |
| | 111 | 126 | 276 | 285 |
| | | | | 262 |
| | | | | 57 |
| PstI | 292 | 292 | 425 | 402 |
| | 284 | 283 | 151 | 155 |

TABLE 1D

Primer Set DG152–DG153 (Seq ID Nos. 11 and 12) and DG148–DG149 (Seq ID Nos. 18 and 19)

To obtain the results in this Table, chromosomal DNA was originally amplified with the listed primers. The PCR products were extracted with chloroform, phenol/chloroform, and ether, desalted over a biogel P-4 spin column and electrophoresed on a 3% NuSieve ™ GTG low melting agarose gel. The desired band was cut out of the gel, extracted with phenol and then with ether, and desalted over a biogel P-4 spin column. A sample of the purified band was reamplified with the listed primers, and the products of this latter PCR were used in the restriction analysis.

| Enzyme | Taq Expected | Taq Experimental | sps17 Expected | sps17 Experimental |
|---|---|---|---|---|
| Undigested | 279 | 320 | 279 | 300 |
| ApaI | 210 | 230 | 207 | 215 |
| | 69 | 80 | 72 | 71 |
| BanI | 141 | 150 | 244 | 252 |
| | 138 | 150 | 35 | 34 |
| KpnI | 141 | 150 | 279 | 280 |
| | 138 | 150 | | |
| SmaI | 242 | 252 | 152 | 160 |
| | 37 | 39 | 87 | 91 |
| | | | 40 | 38 |
| XhoI | 279 | 280 | 279 | 275 |

TABLE 1E

Primer Set DG150–DG151 (Seq. ID Nos. 20 and 21) to DG148–DG149 (Seq ID Nos. 18 and 19)

The same procedure as set forth above in Table 1D was also used to obtain the results in this Table.

| Enzyme | Taq Expected | Taq Experimental | sps17 Expected | sps17 Experimental |
|---|---|---|---|---|
| Undigested | 435 | 430 | 435 | 450 |
| ApaI | 294 | 300 | 294 | 310 |
| | 72 | 76 | 72 | 74 |
| | | | 69 | |
| BanI | 297 | 302 | 400 | 400 |
| | 138 | 145 | 35 | 36 |
| KpnI | 297 | 300 | 435 | 430 |
| | 138 | 143 | | |
| SmaI | 242 | 250 | 308 | 172 |
| | 157 | 168 | 87 | 97 |
| | 37 | 39 | 40 | 43 |
| XhoI | 286 | 300 | 435 | 430 |
| | 149 | 160 | | |

TABLE 1F

Primer Set DG164–DG167 (Seq ID Nos. 22–25) to DG181–DG182 (SeQ ID Nos, 28 and 29)

The same procedure as set forth above in Table 1D was also used to obtain the results in this Table.

| Enzyme | Taq Expected | Taq Experimental | sps17 Expected | sps17 Experimental |
|---|---|---|---|---|
| Undigested | 139 | 160 | 139 | 151 |
| AvaI | 76 | 86 | 79 | 84 |
| | 63 | 73 | 60 | 70 |
| BanI | 122 | 150 | 119 | 127 |
| | 17 | not detected | 20 | not detected |
| HpaII | 76 | 91 | 78 | 83 |
| | 63 | 72 | 61 | 70 |
| MboII | 63 | 60 | 70 | 70 |
| | 59 | 58 | 43 | 18 |
| | 17 | 18 | 24 | |
| SmaI | 76 | 91 | 79 | 87 |
| | 63 | 72 | 60 | 72 |

TABLE 1G

Primer Set DG164–DG167 (Seq ID Nos. 22–25) to DG160–DG167 (Seq ID Nos. 30–33 and 22–25)

The same procedure set forth above in Table 1D was also used to obtain the results in this Table.

| Enzyme | Taq Expected | Taq Experimental | sps17 Expected | sps17 Experimental |
|---|---|---|---|---|
| Undigested | 220 | 212 | 220 | 230 |
| AvaI | 157 | 170 | 160 | 157 |
| | 63 | 74 | 60 | 74 |
| BanI | 122 | 130 | 118 | 130 |
| | 98 | 106 | 102 | 110 |
| HpaII | 157 | 166 | 160 | 160 |
| | 63 | 70 | 61 | 72 |
| SmaI | 157 | 170 | 160 | 178 |
| | 63 | 71 | 60 | 73 |

TABLE 1H

Primer Set DG124–DG125 (Seq ID Nos. 7 and 8) to DG130–DG131 (Seq ID Nos. 16 and 17)

The same procedure set forth above in Table 1D was also used to obtain the results in this Table.

| Enzyme | Taq Expected | Taq Experimental | sps17 Expected | sps17 Experimental |
| --- | --- | --- | --- | --- |
| Undigested | 195 | 225 | 195 | 208 |
| ApaI | 126 | 138 | 111 | 123 |
|  | 69 | 74 | 84 | 99 |
| AvaI | 121 | 138 | 195 | 208 |
|  | 74 | 86 |  |  |
| BalI | 195 | 210 | 195 | 208 |
| HpaII | 107 | 122 | 109 | 128 |
|  | 57 | 64 | 48 | 56 |
|  | 22 | 24 | 25 | 27 |
|  | 9 | 17 | 13 | 23 |

TABLE 1I

Primer Set DG100–DG101 (Seq ID Nos. 9 and 10) to DG130–DG131 (Seq ID Nos. 16 and 17)

The same procedure set forth above in Table 1D was also used to obtain the results in this Table.

| Enzyme | Taq Expected | Taq Experimental | sps17 Expected | sps17 Experimental |
| --- | --- | --- | --- | --- |
| Undigested | 540 | 520 | 543 | 520 |
| ApaI | 414 | 435 | 432 | 445 |
|  | 126 | 140 | 111 | 122 |
| AvaI | 419 | 440 | 353 | 362 |
|  | 121 | 138 | 190 | 200 |
| BalI | 393 | 390 | 543 | 520 |
|  | 147 | 158 |  |  |

TABLE 1J

Primer Set DG152–DG153 (Seq ID Nos. 11 and 12) to DG126–DG127 (Seq ID Nos. 34 and 35)

To obtain the results in this Table, chromosomal DNA was amplified with the listed primer set, and the PCR product was directly analyzed by restriction analysis.

| Enzyme | Taq Expected | Taq Experimental | sps17 Expected | sps17 Experimental |
| --- | --- | --- | --- | --- |
| Undigested | 624 | 610 | 627 | 590 |
| ApaI | 417 | 430 | 420 | 430 |
|  | 207 | 220 | 207 | 220 |
| KpnI | 486 | 470 | 627 | 590 |
|  | 138 | 148 |  |  |
| HindIII | 349 | 360 | 627 | 590 |
|  | 275 | 290 |  |  |

EXAMPLE 3

Cloning the Thermus Species sps17 (Tsps17) DNA Polymerase Gene

This Example describes the strategy and methodology for cloning the Tsps17 DNA polymerase (Tsps17 Pol I) gene of Thermus species sps17.

I. Cloning PCR products

A. DG140–DG141 (Seq ID Nos. 5 and 6) and MK131 (Seq ID No. 15) (clones 16-6, 16-9)

1. Initial PCR

Tsps17 chromosomal DNA (10 ng) was initially amplified using DG136–DG137 (Seq ID Nos. 39 and 40) and DG168–DG169 (Seq ID Nos. 41 and 13) (50 pmoles each) yielding a series of products. (The expected 922 base pair product based on the Taq sequence was not clearly evident). A sample of the PCR product (1/100 and 1/1000) was amplified using DG140–DG141 (Seq ID Nos. 5 and 6) and MK131 (Seq ID No. 15) (50 pmoles each). The identity of the major product was confirmed by digestion using SacI, BamHI, and PstI restriction endonucleases. BamHI, SacI, and PstI gave unique patterns as indicated in Table 1C.

2. Preparation of the fragments for cloning

The PCR product was extracted first with chloroform, then with phenol/chloroform, and desalted over a biogel P-4 spin column. The ends of the fragments were made blunt-ended by treatment with DNA polymerase I, Klenow fragment (5 units at room temperature for 42 minutes according to the manufacturer's specifications), extracted with phenol/chloroform and ether, and desalted over a biogel P-4 spin column. The 5' ends were then phosphorylated using T4 polynucleotide kinase (20 units at 37° C. for 1.5 hours). The samples were extracted with phenol/chloroform and ether, desalted over a biogel P-4 spin column, restricted with BglII (16 units at 37° C. for 1.5 hours), reextracted with phenol/chloroform and then ether, and desalted over a biogel P-4 spin column.

3. Preparation of a vector for cloning

Vector pBSM13+HindIII::BglII (10 μg) was restricted with 30 units of SmaI at room temperature for 1 hour followed by restriction with 16 units of BglII at 37° C. for 2.5 hours. The ends were dephosphorylated by treatment with bacterial alkaline phosphatase at 37° C. for 1 hour. The sample was extracted with phenol/chloroform and then with ether and dephosphorylated over a biogel P-4 spin column.

Vector pBSM13+(purchased from Stratagene) was used to make vector pBSM13+HindIII::BglII by digesting vector pBSM13+ with restriction enzyme HindIII, blunting the ends of the digested vector by Klenow treatment, ligating BglII linkers (5'CAGATCTG), transforming host cells, and selecting transformants which contained a plasmid identical to pBSM13+ but for the absence of a HindIII site and the presence of a BglII site.

4. Ligation and screening

The prepared vector (0.3 μg) was ligated to the prepared PCR product (one-fifth) using 400 units of T4 DNA ligase and 10 units of T4 RNA ligase at 10° C. for 14 hours followed by transformation into DG98. Transformants were selected on ampicillin containing agar plates. Plasmid DNA from twenty ampicillin-resistant clones was screened by restriction analysis. Digestion with EcoRI and BglII identified 7 candidates (clones 16-2, 16-3, 16-6, 16-9, 16-13, 16-16, and 16-20). The correct clones were further identified by restriction with EcoRI and PstI, and BglII and BamHI.

5. Sequence analysis

A 0.1 ml sample of a 10 ml overnight culture was inoculated into 10 ml of R2-7, 250 μg/ml methicillin and grown at 37° C. until the OD$_{600}$ reached 0.2. A 1.5 ml sample of each culture was infected with R408 helper phage at an MOI of 10 and the incubation continued at 37° C. for an additional 4–5 hours. The phage were precipitated by incubation in 0.4M NaCl, 29% PEG (8,000) at 4° C. for 16 hours. Following centrifugatoin, the pellets were resuspended in 100 μl of 10 mM Tris-HCl, 0.1 mM EDTA, pH 8, phenol extracted, and ethanol precipitated. The DNA was then resuspended in 10 mM Tris-HCl, 0.1 mM EDTA, pH 8, and used for sequencing by the method of Sanger, using the Sequenase TM kit.

B. DG157 and DG169 (Seq ID Nos. 3 and 13) (clones 32-1 and 32-34)

1. Initial PCR and preparation of fragments for cloning

Tsps17 chromosomal DNA (10 ng) was amplified using DG157 (Seq ID No. 3) and DG169 (Seq ID No. 13) (50 pmoles each), extracted with chloroform, and desalted over a biogel P-4 spin column. The correct product was purified following electrophoresis on a 1% NuSieve TM GTG low melting agarose gel. The amount of desired product was increased by reamplification of 1/3000 and 1/30,000 of the purified fragment with the same primers. The PCR products were extracted with chloroform and then with phenol/chloroform, desalted over a biogel P-4 spin column, restricted with EcoRI and BglII (40 units each at 37° C. for 2 hours), extracted with phenol/chloroform and ether, and concentrated and desalted over a biogel P-4 spin column. The desired fragment was purified following electrophoresis on a 1% NuSieve TM GTG agarose gel, extracted with phenol and then with ether, and concentrated and desalted over a biogel P-4 spin column.

2. Preparation of a vector for cloning

Vector pBSM13+HindIII::BglII (62.5 μg) was digested with BglII (80 units at 37° C. for 3 hours) and then EcoRI (100 units for 2.5 hours). The preparation was dephosphorylated with bacterial alkaline phosphatase at 37° C. for 4 hours, extracted with phenol/chloroform and then with ether, and desalted over a biogel P-4 spin column.

3. Ligation and screening

The prepared vector (0.4 μg) was ligated with fragment (1/100) using 400 units of T4 DNA ligase at 10° C. for 22 hours and the preparation transformed into DG98. Transformants were selected on ampicillin-containing agar plates. Twenty ampicillin-resistant colonies were grown up in liquid broth, and the DNA was isolated and analyzed by restriction analysis. Restriction with EcoRI and BglII gave the expected size of insert. The identity of the clones was further confirmed by restriction with BglII and SacI

4. Sequence analysis

A 0.1 ml sample of a fresh overnight culture was grown in R2-7, 250 μg/ml methicillin at 37° C. until an O.D.$_{600}$ of 0.2. The cultures were infected with R408 helper phage at an MOI of 10 and the cultures grown an additional 5 hours at 37° C. Single strand DNA was isolated by precipitating phage from 1.3 ml of supernatant after centrifugation of 1.5 ml of culture with 0.4M NaCl, 29% PEG (8000) at 4° C. for 16 hours. Following centrifugation, the pellets were resuspended in 100 μl of 10 mM Tris-HCl, 0.1 mM EDTA, pH 8, phenol extracted, ethanol precipitated, and the DNA resuspended in 20 μl of 10 mM Tris-HCl, 0.1 mM EDTA, pH 8. The DNA from clone 32-4 was sequenced by the method of Sanger, using the Sequenase TM kit.

II. Mapping restriction sites in the chromosome

A. Preparation of a Southern filter

Tsps17 chromosomal DNA (2.9 ng) was digested with restriction endonucleases AatII (2 units), AccI (10 units), BanI (25 units), HindIII (20 units), NheI (4 units), or XmnI (6 units) at 37° C. for 5 hours followed by electrophoresis on a 0.7% agarose gel along with radioactively labeled HindIII-digested lambda DNA as a molecular weight marker. The DNA was transferred to GeneTrans TM nitrocellulose paper by capillary action with 400 mM NaOH for 18 hours. The membranes were rinsed in 2×SSC and the DNA was cross-linked to the nitrocellulose by UV irradiation with a Stratalinker TM 1800 and subjected to prehybridization in 6×SSC, 0.1% SDS, 5×Denhardt's, 50 mM sodium phosphate, pH 7, and 210 μg/ml sonicated calf thymus DNA at 45° C. for 2 hours.

B. Preparation of probe

A gel purified PCR fragment (1/1000) derived from Tsps17 using DG169 (Seq ID No. 13) and DG157 (Seq ID No. 3) was amplified using the same primers in the presence of 200 μM each of dATP, dCTP, and dTTP, 40 μM dGTP, and 70 μCi of alpha-$^{32}$P-dGTP. The radioactively labeled PCR product was gel purified following electrophoresis on a 3% NuSieve TM GTG low melting agarose gel, phenol extracted, and ether extracted.

C. Hybridization and wash

The filter was hybridized in 6.25×SSC, 0.1% SDS, 5×Denhardt's, 50 mM sodium phosphate, pH 7.0, and 40 μg/ml carrier sonicated heat-denatured calf thymus DNA with 4×10$^6$ CPM of probe at 52° C. for 14 hours. The filter was washed twice at 50° C. for 40 to 150 minutes in 5×SSC, 0.1% SDS, and autoradiographed.

D. Results

Size fragments which hybridized to product DG157/DG169 (Seq ID No. 3/Seq ID No. 13):

| Restriction Enzyme | Size fragments (base pairs) |
| --- | --- |
| AatII | 24,000; 3,100 |
| AccI | 3,75; 2,850 |
| BanI | 1,550 (expected 1682) |
| HindIII | 3,300 |
| NheI | 25,000 |
| XmnI | 1,500 (expected 1685) |

Due to the low stringency of the wash, some of these fragments may be cross-hybridizing fragments. From the final sequence, the pattern of chromosomal mapping seen with BanI and XmnI is correct.

III. Second mapping of restriction sites in chromosome

A. DG148–DG149 (Seq ID Nos. 18 and 19) and DG152–DG153 (Seq ID Nos. 11 and 12)

1. Preparation of transfer

Tsps17 chromosomal DNA (1 μg) was digested with ApaLI, NaeI, PvuII, and SacI, electrophoresed on a 0.7% agarose gel with radio-labeled DNA HindIII-digested lambda as a molecular weight marker, acid nicked with 0.25N HCl for 22 minutes and transferred to HybondN+ TM nylon with 0.4M NaOH by capillary action for 21 hours. The DNA was cross-linked to the filter using the Stratalinker TM set at 50 mjoules and incubated with prehybridization solution at 65° C. for 1.5 hours.

2. Preparation of the probe (DG148–DG149 [Seq ID Nos. 18 and 19] and DG152–DG153 [Seq ID Nos. 11 and 12])

Tsps17 chromosomal DNA (10 ng) was amplified with DG152–DG153 (Seq ID Nos. 11 and 12) and DG148–DG149 (Seq ID Nos. 18 and 19). The PCR product was extracted with chloroform, phenol/chloroform, and ether, desalted over a biogel P-4 spin column, and the PCR fragment purified following electrophoresis on a 3% NuSieve TM GTG low melting agarose gel. The fragment was extracted with phenol and then with ether, and concentrated and desalted over a biogel P-4 spin column. The fragment was confirmed by restriction enzyme analysis using MboII, AvaI, BanI, HpaII, and SmaI (see Table 1D). The PCR product gave similar digestion patterns as the analogous Taq product with ApaLI, and XhoI but differed in the pattern with BanI, KpnI, and SmaI. To prepare labeled probe, a portion (1/1000) of the purified fragment was amplified with DG148–DG149 (Seq ID Nos. 18 and 19) and DG152–DG153 (Seq ID Nos. 11 and 12) in the presence of 200 μM each of dATP, dCTP, and dTTP and 40 μM dGTP (50 μCi). The radioactively labeled fragment was purified following electrophoresis on a 3% NuSieve ™ GTG low melting agarose gel, extracted with phenol and then with ether, and concentrated and desalted over a biogel P-4 spin column.

3. Hybridization and autoradiography

The filter was hybridized to $6 \times 10^5$ CPM of probe at 65° C. for 25 hours, washed in 2×SSPE, 0.1% SDS at 65° C. for 10 minutes, 1×SSPE, 0.1% SDS at 65° C. for 24 minutes, and autoradiographed.

4. Results

| Restriction Enzyme | Size band using DG148–DG149 (Seq ID Nos. 18 and 19) and DG152/DG153 (Seq ID Nos. 11 and 12) |
|---|---|
| ApaLI | 6,300 bp |
| NaeI | 10,300 bp |
| PvuII | 8,300 bp |
| SacI | 2,620 bp |

B. DG160–DG163 (Seq ID No. 30–33) and DG164–DG167 (Seq ID No. 22–25)

1. Preparation of membrane

The previous probe was removed by boiling the membrane in 0.5% SDS.

2. Preparation of probe (DG160–DG163 [Seq ID No. 30–33] and DG164–DG167 [Seq ID No. 22–25])

Tsps17 chromosomal DNA (10 ng) was amplified with DG160–DG163 (Seq ID No. 30–33) and DG164–DG167 (Seq ID No. 22–25). The PCR product was extracted with chloroform, phenol/chloroform, and ether, desalted over a biogel P-4 spin column, and the PCR fragment purified following electrophoresis on a 3% NuSieve ™ GTG low melting agarose gel. The fragment was extracted with phenol and then with ether, and concentrated and desalted over a biogel P-4 spin column. The fragment was identified by restriction enzyme analysis with MboII, AvaI, BanI, HpaII, and SmaI (see Table 1G). The PCR product gave similar digestion patterns as the analogous Taq product with AvaI, BanI, HpaII, and SmaI. To prepare labeled probe, a portion (1/1000) of the purified fragment was amplified with DG164–DG167 (Seq ID No. 22–25) and DG160–DG163 (Seq ID No. 30–33) in the presence of 200 μM each of dATP, dCTP and dTTP and 40 μM dGTP (50 μCi). The radioactive fragment was purified following electrophoresis on a 3% NuSieve ™ GTG low melting agarose gel, extracted with phenol and then with ether, and concentrated and desalted over a biogel P-4 spin column.

3. Hybridization and autoradiography

The filter was hybridized with $5.4 \times 10^5$ CPM of the probe at 67° C. for 19 hours, washed in 1×SSPE, 0.1% SDS at 23° C. for 42 minutes, 1×SSPE, 0.1% SDS at 23° C. for 13 minutes, 1×SSPE, 0.1% SDS at 65° C. for 44 minutes, and autoradiographed.

4. Results

| Restriction Enzyme | Size band using DG148–DG149 (Seq ID Nos. 18 and 19) and DG152–DG153 (Seq ID Nos. 26 and 27) |
|---|---|
| ApaLI | 6,200 bp |
| NaeI | 3,920 bp |
| PvuII | 1,620 bp |
| SacI | 3,000 bp |

IV. Third mapping of restriction sites in chromosome

A. DG160–DG163 (Seq ID No. 30–33) and DG164–DG167 (Seq ID No. 22–25)

1. Preparation of blot;

Tsps17 chromosomal DNA (1 μg) was digested with AccI, BamHI, BglII, EcoRI, KpnI, PstI, SalI, SphI, or XbaI at 37° C. for 27 hours and electrophoresed on a 0.7% agarose gel. The gel was treated with 0.25N HCl for 27 minutes, and the DNA was transferred to HybondN+ ™ nylon membrane using 0.4N NaOH by capillary action. The DNA was cross-linked to the membrane using the Stratalinker ™ 1800 at 40 mjoules, and treated with prehybridization buffer at 65° C. for 4 hours.

2. Preparation of probe (DG160–DG163 [Seq ID Nos. 30–33] and DG164–DG167 [Seq ID Nos. 22–25])

Tsps17 chromosomal DNA (10 ng) was amplified with DG160–DG163 (Seq ID Nos. 30–33) and DG164–DG167 (Seq ID Nos. 22–25). The PCR product was extracted with chloroform, phenol/chloroform, and ether, desalted over a biogel P-4 spin column, and the PCR fragment purified following electrophoresis on a 3% NuSieve ™ GTG low melting agarose gel. The fragment was extracted with phenol and then with ether, and concentrated and desalted over a biogel P-4 spin column. The fragment was confirmed by restriction analysis using AvaI, BanI, HpaII, and SmaI. The PCR product gave similar digestion patterns as the analogous Taq product with AvaI, BanI, HpaII, and SmaI. To prepare labelled probe, a portion (1/1000) of the purified fragment was amplified with DG164–DG167 (Seq ID Nos. 22–25) and DG160–DG163 (Seq ID No. 30–33) in the presence of 200 μM each of dATP, dCTP, and dTTP and 40 μM dGTP (50 μCi). The radioactively labeled fragment was purified following electrophoresis on a 3% NuSieve ™ GTG low melting agarose gel, extracted with phenol and then with ether, and concentrated and desalted over a biogel P-4 spin column.

3. Hybridization and autoradiography

The membrane was hybridized to $2.5 \times 10^6$ CPM probe at 65° C. for 21 hours and washed twice in 2×SSPE, 0.1% SDS at 23° C. for 10 minutes, and 1×SSPE, 0.1% SDS at 67° C. for 18 minutes, and autoradiographed.

4. Results

| Restriction Enzyme | Size of fragment hybridized to DG160–DG163 (Seq ID Nos. 30–33) and DG164–DG167 (Seq ID Nos. 22–25) |
|---|---|
| AccI | 3,950 bp |
| BamHI | 8,400 bp |
| BglII | 18,000 bp |
| EcoRI | >23,000 bp |
| KpnI | 5,200 bp |
| PstI | 10,000 bp |
| SalI | >23,000 bp |
| SphI | >20,000 bp |

-continued

| Restriction Enzyme | Size of fragment hybridized to DG160–DG163 (Seq ID Nos. 30–33) and DG164–DG167 (Seq ID Nos. 22–25) |
|---|---|
| XbaI | >23,000 bp |

B. DG148–DG149 (Seq ID Nos. 18 and 19) and DG152–DG153 (Seq ID Nos. 26 and 27)

1. Preparation of the membrane

The previous probe was removed by boiling the membrane in 0.5% SDS.

2. Preparation of probe (DG148–DG149 [Seq ID Nos. 18 and 19] and DG152–DG153 [Seq ID Nos. 26 and 27])

Tsps17 chromosomal DNA (10 ng) was amplified with DG152–DG153 (Seq ID Nos. 26 and 27) and DG148–DG149 (Seq ID Nos. 18 and 19). The PCR product was extracted with chloroform, phenol/chloroform, and ether, desalted over a biogel P-4 spin column, and the PCR fragment purified following electrophoresis on a 3% NuSieve TM GTG low melting agarose gel. The fragment was extracted with phenol and then with ether, and concentrated and desalted over a biogel P-4 spin column. The fragment was confirmed by restriction analysis using MboII, AvaI, BanI, HpaII, and SmaI. The PCR product gave similar digestion patterns as the analogous Taq product with ApaLI, and XhoI, but differed in the pattern with BanI, KpnI, and SmaI. To prepare labelled probe, a portion (1/100) of the purified fragment was amplified with DG148–DG149 (Seq ID Nos. 18 and 19) and DG152–DG153 (Seq ID No. 26 and 27) in the presence of 200 μM each of dATP, dCTP and dTTP and 40 μM dGTP (50 μCi). The radioactively labeled fragment was purified following electrophoresis on a 3% NuSieve TM GTG low melting agarose gel, extracted with phenol then ether, and concentrated and desalted over a biogel P-4 spin column.

3. Hybridization and autoradiography

The membrane was hybridized to $1.89 \times 10^6$ CPM of probe at 65° C. for 18 hours, washed twice in 2×SSPE, 1% SDS at 23° C. for 11–14 minutes and 1×SSPE, 0.1% SDS at 65° C. for 15 minutes, and autoradiographed.

4. Results

| Restriction Enzyme | Size of fragment hybridized to DG160–DG163 (Seq ID Nos. 30–33) and DG164–DG167 (Seq ID Nos. 22–25) |
|---|---|
| AccI | 4,050 bp |
| BamHI | 1,700 bp, 1,170 bp, and 1,020 bp |
| BglII | 19,000 bp, weak 4,500 bp |
| EcoRI | >23,000 bp |
| KpnI | 5,200 bp |
| PstI | 4,400 bp |
| SalI | >23,000 bp |
| SphI | >23,000 bp weak 13,600 bp and 7,300 bp |
| XbaI | >23,000 bp |

V. Cloning restriction fragments from the chromosome

A. KpnI fragment containing the entire gene

1. Restriction, fractionation, and purification

Tsps17 chromosomal DNA (20 μg) was digested with restriction endonuclease Asp718 (110 units) at 37° C. for 18 hours. The completeness of the restriction digest was confirmed by electrophoresis of a sample of the digest on a 0.7% agarose gel, transfer to HybondN+ TM nylon membrane, and probing with a TZO5 probe from DG152–DG153 (Seq ID Nos. 26 and 27) to DG148–DG149 (Seq ID No. 18 and 19) and a TZO5 probe from DG160–DG163 (Seq ID No. 30–33) to DG164–DG167 (Seq ID No. 22–25). The restriction digest was size fractionated a 1% agarose/1% NuSieve TM GTG agarose gel in TEA, and 500 μl fractions were collected. Samples of selected fractions were concentrated and run on a 0.7% agarose gel. This analytic gel was nicked with 0.25N HCl for 15 minutes and transferred to HybondN+ TM nylon membrane by capillary action in 0.4N NaOH for 17 hours at room temperature. The DNA was cross-linked to the membrane using the Stratalinker TM 1800 at 50 mjoules. The membranes were treated in prehybridization buffer for 2.7 hours at 65° C. and hybridized to a TZO5 probe from DG157 (Seq ID No. 3) and DG169 (Seq ID No. 13) at 65° C. for 23 hours. Following washing, the membranes were autoradiographed. The major portion of the Asp718 fragment hybridizing to the probe was in fraction 13.

2. Preparation of vector

Vector pBSM13+ (5 μg) was digested with Asp718 (20 units) at 37° C. for 18 hours, dephosphorylated with bacterial alkaline phosphatase at 37° C., extracted with phenol/chloroform and then with ether, and desalted over a biogel P-4 spin column.

3. Cloning and screening

Fractions 11 to 15 from the size fractionation were concentrated, desalted over a biogel P-4 spin column and ligated to vector at a ratio of insert to vector of 2.5:1 at 4° C. using T4 DNA ligase. Following transformation of a portion of the ligation mixture (½) into DG98, the cells were plated onto R-4 agar plates containing 50 μg/ml ampicillin. Colonies were lifted onto nitrocellulose filters, lysed in triton lytic mixture, the DNA denatured in 0.5N NaOH, 1 mM EDTA, neutralized in 0.5M Tris, 1.0M NaCl, pH 8, and rinsed in 0.3M NaCl, 10 mM Tris, 1 mM EDTA, pH 7.6. Following baking for 2 hours at 80° C. under a vacuum, the filters were treated in prehybridization mixture at 65° C. for 1 hour. The filters were then hybridized with a TZO5 probe extending between DG157 (Seq ID No. 3) and DG169 (Seq ID No. 13) at 65° C. for 18 hours. The membranes were washed in 5×SSC, 0.1% SDS at 23° C. for 15 minutes, 2×SSC, 0.1% SDS at 23° C. for 20 minutes, and autoradiographed. Probe-positive colonies were inoculated into R2-7, 250 μg/ml methicillin and grown at 37° C.

Plasmid DNA was isolated from a sample of cultures by centrifuging 3 ml of cells, resuspension of pellets in 100 μl of 25 mM Tris, pH 8, 50 mM glucose, 10 mM EDTA, and 20 mg/ml lysozyme, followed by incubation at 23° C. for 10 minutes. The cells were lysed by incubation with 200 μl of 0.2N NaOH, 1% SDS at 23° C. for 11 minutes. The SDS was precipitated by incubation with 150 μl of 3M KOAc, pH 4.8, at 4° C. for 30 minutes. Following centrifugation, the supernatant was extracted with phenol/chloroform and ethanol precipitated. The DNA pellet was resuspended in 50 μl of 10 mM Tris, 0.1 mM EDTA, pH 8, 200 μg/ml RNaseA, and 500 units/ml RNase $T_1$.

The size of the insert was identified by restriction of a portion of the plasmid DNA with Asp718 followed by electrophoresis on 0.7% agarose gels. The identity of the insert was further analyzed after desalting over biogel P-4 spin columns. Samples were then restricted with Asp718, BamHI, or PstI followed by electrophoresis on 1% agarose and 10% polyacrylamide gels along with radioactively labeled markers. Clones were identified by the presence of the expected 5 kb and 1653 bp Asp718 fragments.

To analyze and map the insert, the agarose gels were treated with 0.25N HCl for 25 minutes, and transferred to HybondN+ ™ nylon membrane by capillary action using 40 mM NaOH. The DNA was cross-linked to the membrane using a Stratalinker ™ 1800 at 50 mjoules, treated in prehybridization buffer at 65° C. for 1 hour and 25 minutes and hybridized to approximately $2.18 \times 10^5$ CPM of a TZO5 probe extending between DG157 (Seq ID No. 3) and DG169 (Seq ID No. 13) at 65° C. for 22 hours. The filters were washed twice in 2×SSPE, 0.1% SDS at 23° C. for 12 to 26 minutes, 1×SSPE, 0.1% SDS at 65° C. for 16 minutes, and autoradiographed.

For further analysis and orientation, the blots of the restriction digest gels were further investigated. The previous probe was removed by boiling the blots in 0.1% SDS. The membranes were hybridized to a second TZO5 probe extending between DG160–DG163 (Seq ID Nos. 30–33) and DG164–DG167 (Seq ID Nos. 22–25) (approximately $5 \times 10^5$ CPM) at 65° C. for 18 hours. The filters were washed twice in 2×SSPE, 0.1% SDS at 23° C. for 11 to 13 minutes, 1×SSPE, 0.1% SDS at 65° C. for 20 minutes, and autoradiographed. The clones which reacted with both probes include: 3-7 (weakly with the second probe), 4-13, 4-14, and 4-16.

4. Preparation of DNA for sequence analysis

A sample (0.1 ml) of overnight cultures from clones 3-7, 4-13, 4-14, and 4-16 was inoculated into 10 ml of R2-4 media, 250 µg/ml methicillin and grown at 37° C. to an O.D.$_{600}$ of 0.2. The cultures were infected with R408 helper phage at an MOI of 10 and the incubation continued an additional 5 hours. Single strand phage DNA was isolated as previously described.

Plasmid DNA was isolated as described above for screening. The identity of the clones were confirmed following restriction with EcoRI or EcoRI and Asp718.

Because of plasmid instability, the fragments were transferred from clones 4-13, 4-14 and 4-16 into both pBR322 and pUC13 as oriented EcoRI-HindIII fragments. These clones gave good DNA yields. The clones were analyzed by restriction digestion with EcoRI, BglII, HindIII, EcoRI and BglII, and EcoRI and HindIII.

5. Preparation of vectors

Vectors pUC13 (10 µg) and pBR322 (10 µg) were digested with EcoRI and HindIII, dephosphorylated using bacterial alkaline phosphatase, extracted with phenol/chloroform and then with ether, and desalted over a biogel P-4 spin column.

6. Ligation, transformation, cloning and screening

Clones 4-13 and 4-14 were restricted with EcoRI and HindIII and the Tsps17 fragment purified following electrophoresis on a 1% NuSieve ™ GTG low melting agarose gel. The fragments were ligated to both cloning vectors at a ratio of insert to vector of 2:1 and transformed into DG98. Selected ampicillin-resistant colonies were grown and screened as previously described by standard techniques. The few clones selected were grown in liquid culture, their plasmid DNA isolated by standard protocols, and the insert identified by digestion with Asp718. The clones contained the desired insert. (pUC13 clones: from 4-13: 48-1 to 10; from pBSM13+ clone 4-14: 49-1 to 10; pBR322 clones: from pBSM13+ clone 4-13: 44-1 to 10; and from pBSM13+ clone 4-14: 45-1 to 10).

7. Preparation of plasmid for sequencing

Three pUC clones 48-4 (from pBSM13+ clone 4-13), 49-3 and 49-7 (from pBSM13+ clone 4-14) were grown in 50 µg/ml ampicillin, 250 µg/ml of methicillin in R2-4 media (1 liter), grown to an O.D.$_{600}$ of 0.46, and amplified overnight with 150 µg/ml chloramphenicol. The cultures were centrifuged, washed in 0.9% NaCl, resuspended in 15 ml of 50 mM Tris, pH 8.0, 25% sucrose to which was added 4 ml of 0.6M EDTA, pH 8, and 5 ml of 20 mg/ml lysozyme (in 10 mM Tris, 0.1 mM EDTA, pH 9). The samples were quickly frozen in a dry-ice ethanol bath for 1 hour, then thawed at 37° C. RNase A was added to a final concentration of 20 µg/ml and RNase T$_1$ to 500 units/ml and the samples incubated at 23° C. for 2 hours. Following centrifugation in a VTi rotor at 45,000 rpm at 5° C. for 2.5 hours, the supernatant was isolated, incubated at 65° C. for 0.5 hours, and the precipitate removed by centrifugation. An equal weight per final volume of cesium chloride was added together with ethidium bromide (0.03×volume supernatant and 0.008×gm CsCl of 5 mg/ml ethidium bromide). After complete suspension of the cesium chloride, the samples were centrifuged in a VTi50 rotor at 45,000 rpm at 25° C. for 40 hours. The lower band corresponding to the plasmid was isolated, extracted with isoamyl alcohol saturated with cesium chloride, and the plasmid isolated by ethanol precipitation. The identity of the plasmid was checked by restriction of a sample with Asp718 followed by electrophoresis on a 0.7% agarose gel.

8. Mapping restriction sites in the chromosome

Labeled PCR products corresponding to the 5' region of the DNA polymerase gene (DG148-DG149 [Seq ID Nos. 18 and 19] and DG152-DG153 [Seq ID Nos. 11 and 12]) and to the 3' region (DG160-DG163 [Seq ID Nos. 30-33] and DG164-DG167 [Seq ID Nos. 22-25]) were used as probes in Southern transfers of Tsps17 chromosomal DNA digested with AatII, AccI, BanI, HindIII, NheI, XmnI, ApaLI, NaeI, PvuII, SacI, BamHI, BglII, EcoRI, KpnI (Asp718), PstI, SalI, SphI, and XbaI. Of the restriction enzymes investigated, KpnI (Asp718) appears to be the most convenient. Digestion of Tsps17 chromosomal DNA yields a 5200 base pair KpnI fragment which hybridizes to both the 5' and 3' probes and therefore comprises Tsps17 DNA polymerase coding sequences.

EXAMPLE 4

Construction of Tsps17 DNA Polymerase Expression Vectors

A number of thermostable Tth DNA polymerase expression vectors are described in the Examples, particularly Example 6, of Ser. No. 455,967, filed Dec. 22, 1989, incorporated herein by reference. These plasmids can be used to place the coding sequence of the sps17 DNA polymerase gene of the present invention in frame for expression under the control of the lambda P$_L$ promoter.

The expression vectors created are then transformed into *E. coli* K12 strain DG116 and cultured under conditions (see Example 7 of Ser. No. 455,967, incorporated herein by reference) that allow for expression of Tsps17 DNA polymerase.

EXAMPLE 5

PCR With Tsps17 DNA Polymerase

About 1.25 units of the Tsps17 DNA polymerase purified in Example 1 is used to amplify rRNA sequences from Tth genomic DNA. The reaction volume is 50 µl, and the reaction mixture contains 50 pmol of primer DG73 (Seq ID No. 36), $10^5$ to $10^6$ copies of the Tth genome ($\sim 2 \times 10^5$ copies of genome/ng DNA), 50 pmol of primer DG74 (Seq ID No. 37), 200 µM of each dNTP, 2 mM MgCl$_2$, 10 mM Tris-HCl, pH 8.3, 50 mM KCl, and 100 µg/ml gelatin (gelatin may be omitted).

The reaction is carried out on a Perkin Elmer DNA Thermal Cycler. Twenty to thirty cycles of 96° C. for 15 seconds; 50° C. for 30 seconds, and 75° C. for 30 seconds are carried out. At 20 cycles, the amplification product (160 bp in size) can be faintly seen on an ethidium bromide stained gel, and at 30 cycles, the product is readily visible (under UV light) on the ethidium bromide stained gel.

The PCR may yield fewer non-specific products if fewer units of Tsps17 DNA polymerase are used (i.e., 0.31 units/50 µl reaction). Furthermore, the addition of a non-ionic detergent, such as laureth-12, to the reaction mixture to a final concentration of 1% can improve the yield of PCR product.

Primers DG73 (Seq ID No. 36) and DG74 (Seq ID No. 37) are shown below:

DG73 5'TACGTTCCCGGGCCTTGTAC 3' (Seq ID No. 36)

DG74 5'AGGAGGTGATCCAACCGCA 3' (Seq ID No. 37)

We claim:

1. A DNA sequence in purified form that encodes the amino acid sequence of Seq ID No. 2, wherein said DNA sequence has been modified to encode a thermostable DNA polymerase that lacks 5'→3' exonuclease activity wherein said modification is a deletion from the N-terminus up to and including the codon encoding an amino acid between amino acids number 43 through 73 inclusively.

2. The DNA sequence of claim 1 that encodes amino acids number 74 to 830 of Seq ID No. 2.

3. The DNA sequence of claim 2 that is nucleotides 1468 to 3735 of Seq ID No 1.

4. A purified DNA sequence that encodes amino acids number 1 to 830 of Seq ID No. 2 wherein at position number 43 an Asp codon is substituted for a Gly codon.

5. The DNA sequence of claim 1 that encodes amino acids number 44 to 830 of SEQ ID No. 2.

6. The DNA sequence of claim 5 that is nucleotides 1378 to 3735 of SEQ ID No. 1.

7. A recombinant DNA vector that comprises the DNA sequence of claim 1.

8. A recombinant host cell transformed with the vector of claim 7.

9. The recombinant host cell of claim 8 that is *E. coli*.

10. A method of producing a Thermus species sps17 DNA polymerase protein comprising:
    (a) culturing a recombinant host cell of claim 8 under conditions such that said protein is expressed, and
    (b) isolating said expressed protein.

11. A method of producing a Thermus species sps17 DNA polymerase protein comprising:
    (a) culturing a recombinant host cell of claim 9 under conditions such that said protein is expressed, and
    (b) isolating said expressed protein.

* * * * *